(12) United States Patent
Fischer et al.

(10) Patent No.: US 6,358,887 B1
(45) Date of Patent: *Mar. 19, 2002

(54) 2-PHENYL-SUBSTITUTED HETEROCYCLIC 1,3-KETONOLS AS HERBICIDES AND PESTICIDES

(75) Inventors: Reiner Fischer, Monheim; Thomas Bretschneider, Lohmar; Hermann Hagemann; Folker Lieb, both of Leverkusen; Norbert Lui, Köln; Michael Ruther, Monheim; Arno Widdig, Odenthal; Christoph Erdelen, Leichlingen; Ulrike Wachendorff-Neumann, Neuwied; Hans-Joachim Santel; Markus Dollinger, both of Leverkusen; Peter Dahmen, Neuss; Norbert Mencke, Leverkusen; Andreas Turberg, Erkrath, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,872
(22) PCT Filed: Jan. 31, 1996
(86) PCT No.: PCT/EP96/00382
§ 371 Date: Aug. 5, 1997
§ 102(e) Date: Aug. 5, 1997
(87) PCT Pub. No.: WO96/25395
PCT Pub. Date: Aug. 22, 1996

(30) Foreign Application Priority Data

Feb. 13, 1995 (DE) .......................................... 195 04 621
Nov. 24, 1995 (DE) .......................................... 195 43 864

(51) Int. Cl.⁷ .................. C07D 207/408; C07D 207/38; C07D 403/12; A01N 43/36
(52) U.S. Cl. ...................... 504/284; 514/409; 548/408; 548/410; 548/411
(58) Field of Search ................. 548/408, 410, 548/411; 504/284; 514/409

(56) References Cited

U.S. PATENT DOCUMENTS 5,258,527 A 11/1993 Krauskopf et al. ......... 548/543

(List continued on next page.)

FOREIGN PATENT DOCUMENTS

EP 442077 8/1991

(List continued on next page.)

*Primary Examiner*—Bruck Kifle
(74) *Attorney, Agent, or Firm*—Norris McLaughlin & Marcus

(57) ABSTRACT

The present invention relates to new compounds of the formula (I)

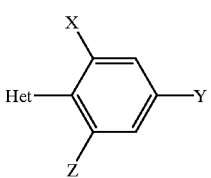

(I)

in which
X, Y and Z have the meanings given in the description and Het represents one of the groups

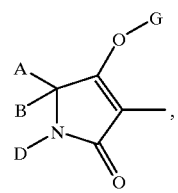

(1)

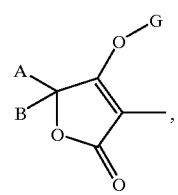

(2)

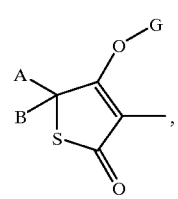

(3)

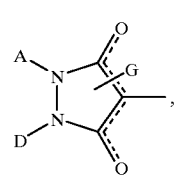

(4)

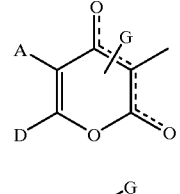

(5)

or (6)

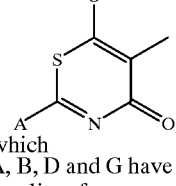

in which
A, B, D and G have the meanings given in the description, a plurality of processes for their preparation, and to their use as pesticides and herbicides.

11 Claims, No Drawings

U.S. PATENT DOCUMENTS

| | | | |
|---|---|---|---|
| 5,262,383 A | 11/1993 | Fischer et al. | 504/195 |
| 5,358,924 A | 10/1994 | Krüger et al. | 504/197 |
| 5,393,729 A | 2/1995 | Fischer et al. | 504/128 |
| 5,462,913 A * | 10/1995 | Fischer et al. | 504/138 |
| 5,504,057 A * | 4/1996 | Fischer et al. | 504/283 |
| 5,567,671 A | 10/1996 | Fischer et al. | 504/283 |
| 5,589,469 A | 12/1996 | Fischer et al. | 514/91 |
| 5,610,122 A | 3/1997 | Fischer et al. | 504/251 |
| 5,616,536 A * | 4/1997 | Fischer et al. | 504/225 |
| 5,622,917 A * | 4/1997 | Fischer et al. | 504/283 |
| 5,677,449 A * | 10/1997 | Fischer et al. | 544/165 |
| 5,811,374 A | 9/1998 | Bertram et al. | 504/246 |

FOREIGN PATENT DOCUMENTS

| | | | |
|---|---|---|---|
| EP | 456063 | | 11/1991 |
| EP | 508126 | | 10/1992 |
| EP | 521334 | | 1/1993 |
| EP | 528156 | | 2/1993 |
| EP | 613 884 | * | 9/1994 |
| EP | 613885 | | 9/1994 |
| EP | 647637 | | 4/1995 |
| WO | WO 95/20572 | * | 8/1995 |
| WO | WO 95/26954 | * | 10/1995 |

* cited by examiner

2-PHENYL-SUBSTITUTED HETEROCYCLIC 1,3-KETONOLS AS HERBICIDES AND PESTICIDES

This application is a 371 of PCT/EP96/00382, which was filed on Jan. 31, 1996.

The invention relates to new phenyl-substituted cyclic ketoenols, to a plurality of processes for their preparation, and to their use as pesticides and herbicides.

Pharmaceutical properties have been previously described of 3-acyl-pyrrolidine-2,4-diones (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-aryl-pyrrolidine-2,4-diones), of which, however, no herbicidal, insecticidal or acaricidal action has been disclosed. Unsubstituted, bicyclic 3-aryl-pyrrolidine-2,4-dione derivatives (EP-A-355 599 and EP-415 211) and substituted monocyclic 3-aryl-pyrrolidine-2,4-dione derivatives (EP-A-377 893 and EP-442 077) having a herbicidal, insecticidal or acaricidal action have been disclosed.

There have also been disclosed polycyclic 3-arylpyrrolidine-2,4-dione derivatives (EP-442 073) and 1H-arylpyrrolidine-dione derivatives (EP-456 063, EP-521 334, EP-596 298, EP-613 884, EP-613 885, WO 94/01 997 and WO 95/01358).

It has been disclosed that certain substituted Δ³-dihydrofuran-2-one derivatives have herbicidal properties (cf. DE-A-4 014 420). The synthesis of the tetronic acid derivatives used as starting compounds (such as, for example, 3-(2-methyl-phenyl)-4-hydroxy-5-(4-fluorophenyl)-Δ³-dihydrofuran-2-one) is also described in DE-A-4 014 420. Compounds of a similar structure without any mention of an insecticidal and/or acaricidal activity are known from the publication Campbell et at., J. Chem. Soc., Perkin Trans. 1, 1985, (8) 1567–76. 3-Aryl-Δ³-dihydrofuranone derivatives having herbicidal, acaricidal and insecticidal properties are furthermore disclosed in EP-528 156 and EP 647 637, but the activity described therein is not always sufficient.

Certain 3H-pyrazol-3-one derivatives, such as, for example, 1,2-diethyl-1,2-dihydro-5-hydroxy-4-phenyl-3H-pyrazol-3-one or {[5-oxo-1,2-diphenyl-4-(p-sulphophenyl)-3-pyrazolin-3-yl]-oxy}-disodium salt or p-(3-hydroxy-5-oxo- 1,2-diphenyl-3-pyrazolin-4-yl)-benzenesulphonic acid are furthermore known from the literature (cf. J. Heterocycl. Chem., 25(5), 1301–1305, 1988 or J. Heterocycl. Chem., 25(5), 1307–1310, 1988 or Zh. Obshch. Khim., 34(7), 2397–2402, 1964). However, a biological action of these compounds is not described.

It is furthermore known that the trisodium salt of 4,4', 4"-(5-hydroxy-3-oxo-1H-pyrazol-1,2,4(3H)-triyl)-tris-benzenesulphonic acid has pharmacological properties (cf. Farmakol. Toksikol. (Moscow), 38(2), 180–186, 1976). However, its use in plant protection is not known.

EP 508 126 and WO 92/16 510 furthermore describe 4-arylpyrazolidine-3,5-dione derivatives having herbicidal, acaridical and insecticidal properties.

Certain phenyl pyrone derivatives which are unsubstituted in the phenyl ring have already been described (cf. A.M. Chirazi, T. Kappe and E. Ziegler, Arch. Pharm. 309, 558 (1976) and K. -H. Boltze and K. Heidenbluth, Chem. Ber. 91, 2849), a possible use of these compounds as pesticides not being mentioned. Phenyl-pyrone derivatives which are substituted in the phenyl ring and have herbicidal, acaricidal and insecticidal properties are described in EP-588 137.

Certain 5-phenyl-1,3-thiazine derivatives which are unsubstituted in the phenyl ring have already been disclosed (cf. E. Ziegler and E. Steiner, Monatsh. 95, 147 (1964), R. Ketcham. T. Kappe and E. Ziegler, J. Heterocycl. Chem. 10, 223 (1973)), a possible use of these compounds as pesticides not being mentioned. 5-Phenyl-1,3-thiazine derivatives which are substituted in the phenyl ring and have a herbicidal, acaricidal and insecticidal action are described in WO 94/14 785.

However, the activity and range of action of these compounds is not always entirely satisfactory, in particular when low rates and concentrations are applied. Furthermore, these compounds are not always sufficiently well tolerated by plants.

There have now been found new compounds of the formula (I)

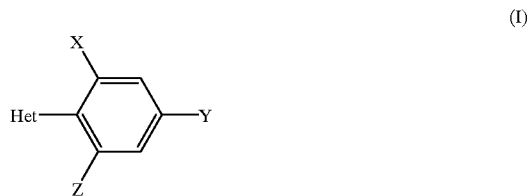

(I)

in which

X represents halogen, alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro, cyano or in each case optionally substituted phenyl, phenoxy, phenylthio, benzyloxy or benzylthio, Y represents hydrogen, halogen, alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro or cyano, Z represents hydrogen, halogen, alkyl, alkenyl, alkinyl, halogenoalkyl, halogenoalkenyl, alkoxy, alkenyloxy, halogenoalkoxy, halogenoalkenyloxy, nitro or cyano, where at least one of the substituents X and Y does not represent halogen, alkyl, halogenoalkyl or alkoxy, Het represents one of the groups

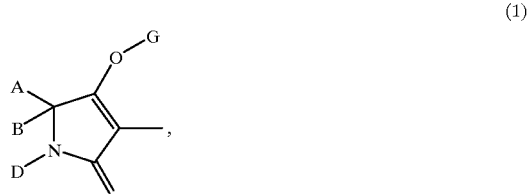

(1)

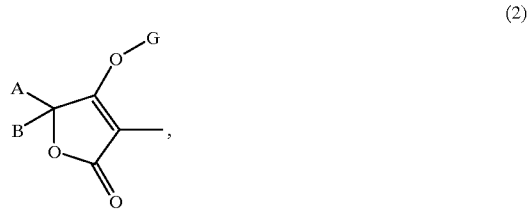

(2)

-continued

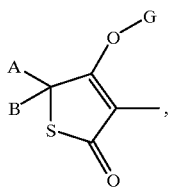
(3)

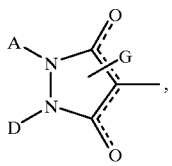
(4)

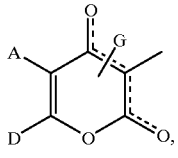
(5)

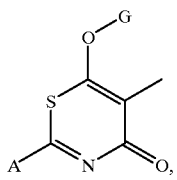
(6)

in which

- A represents hydrogen, or represents alkyl, alkenyl, alkoxyalkyl, polyalkoxyalkyl or alkylthioalkyl, each of which is optionally substituted by halogen, or represents saturated or unsaturated, optionally substituted cycloalkyl in which at least one ring atom is optionally replaced by a hetero atom, or represents aryl, arylalkyl or hetaryl, each of which is optionally substituted by halogen, alkyl, halogenoalkyl, alkoxy, halogenoalkoxy, cyano or nitro,
- B represents hydrogen, alkyl or alkoxyalkyl, or
- A and B together with the carbon atom to which they are bonded represent a saturated or unsaturated, unsubstituted or substituted cycle which optionally contains at least one hetero atom,
- D represents hydrogen or optionally substituted radicals from the series consisting of alkyl, alkenyl, alkinyl, alkoxyalkyl, polyalkoxyalkyl, alkylthioalkyl, saturated or unsaturated cycloalkyl which is optionally interrupted by at least one hetero atom, arylalkyl, aryl, hetarylalkyl or hetaryl, or
- A and D together with the atoms to which they are bonded represent a saturated or unsaturated, unsubstituted or substituted cycle which optionally contains at least one hetero atom,
- G, in the event that Het represents one of the radicals (1), (2), (3), (5) or (6), represents hydrogen (a), or, in the event that Het represents one of the radicals (1), (2), (3), (4), (5) or (6), represents one of the groups

(b)

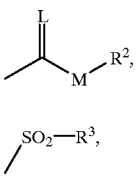
(c)

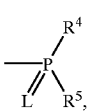
(d)

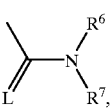
(e)

E or
(f)

(g)

where

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is optionally substituted by halogen, or represents cycloalkyl which can be interrupted by at least one hetero atom and which is optionally substituted by halogen, alkyl or alkoxy, or represents in each case optionally substituted phenyl, phenylalkyl, hetaryl, phenoxyalkyl or hetaryloxyalkyl, $R^2$ represents alkyl, alkenyl, alkoxyalkyl or polyalkoxyalkyl, each of which is optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, each of which is optionally substituted by halogen, and represent in each case optionally substituted phenyl, benzyl, phenoxy or phenylthio, $R^6$ and $R^7$ independently of one another represent hydrogen, or represent alkyl, cycloalkyl, alkenyl, alkoxy or alkoxyalkyl, each of which is optionally substituted by halogen, or represent optionally substituted phenyl, or represent optionally substituted benzyl, or together with the N atom to which they are bonded represent a cycle which is optionally interrupted by oxygen or sulphur.

Depending on the nature of the substituents, the compounds of the formula (I) can also be present in the form of geometric and/or optical isomers or variously composed isomer mixtures, which can optionally be separated in the customary manner. The present invention relates to the pure isomers and also to the isomer mixtures, to their preparation, their use, and to compositions comprising them. However, the following text will always mention compounds of the formula (I), for the sake of simplicity, even though this is to be understood as meaning the pure compounds and, if appropriate, also mixtures containing various proportions of isomeric compounds.

Taking into consideration the meanings (1) to (6) of the Het group, the following main structures (I-1) to (I-6) result.

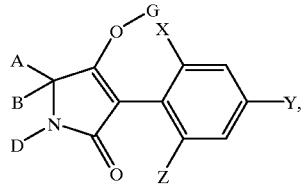
(I-1)

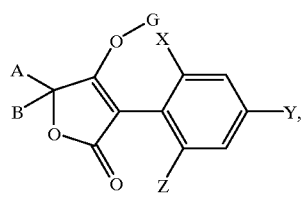
(I-2)

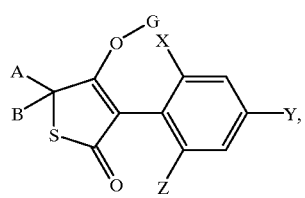
(I-3)

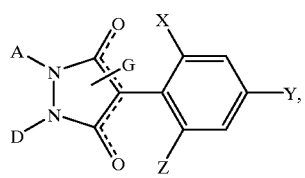
(I-4)

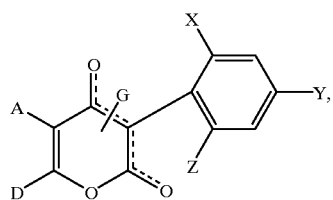
(I-5)

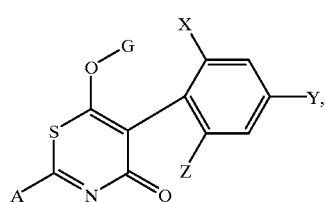
(I-6)

Taking into consideration the various meanings (a), (b), (c), (d), (e), (f) and (g) of group G, the following, main structures (I-1-a) to (I-1-g) result if Het represents group (1)

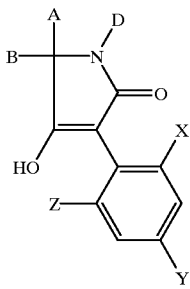
(I-1-a)

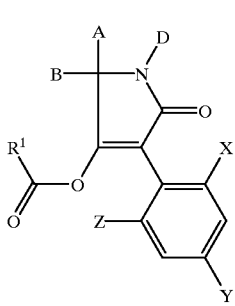
(I-1-b)

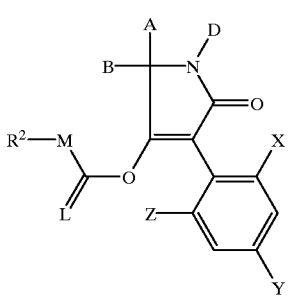
(I-1-c)

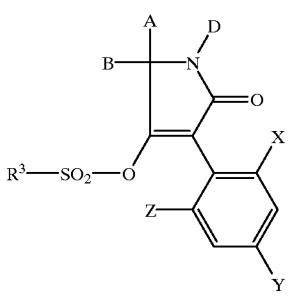
(I-1-d)

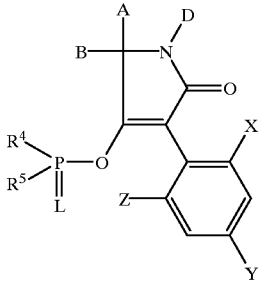
(I-1-e)

in which
A, B, D, G, X, Y and Z have the abovementioned meanings.

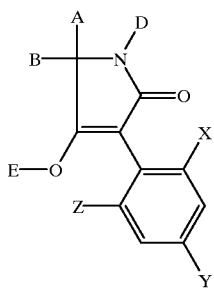

(I-1-f)

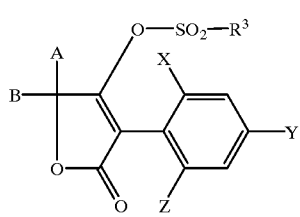

(I-2-d)

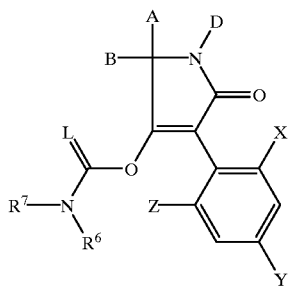

(I-1-g)

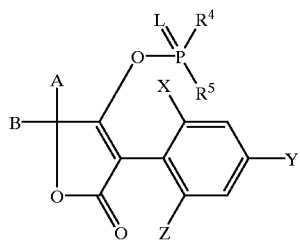

(I-2-e)

in which

A, B, D, E, L, M, X, Y, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G, the following main structures (I-2-a) to (I-2-g) result if Het represents group (2)

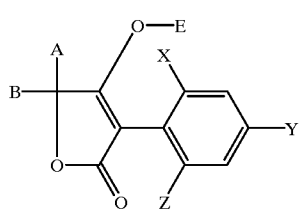

(I-2-f)

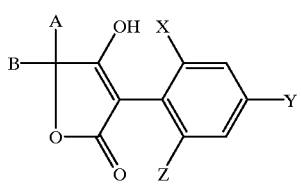

(I-2-a)

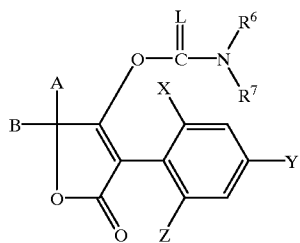

(I-2-g)

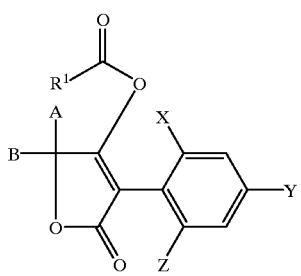

(I-2-b)

in which

A, B, D, E, L, M, X, Y, Z, $R^1$, $R^2$, $R^3$, $R^4$, $R^5$, $R^6$ and $R^7$ have the abovementioned meanings.

Taking into consideration the various meanings (a), (b), (c), (d), (e), (f) and (g) of group G. the following main structures (I-3-a) to (I-3-g) result if Het represents group (3)

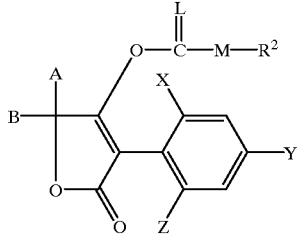

(I-2-c)

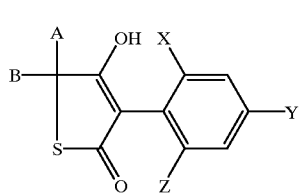

(I-3-a)

-continued

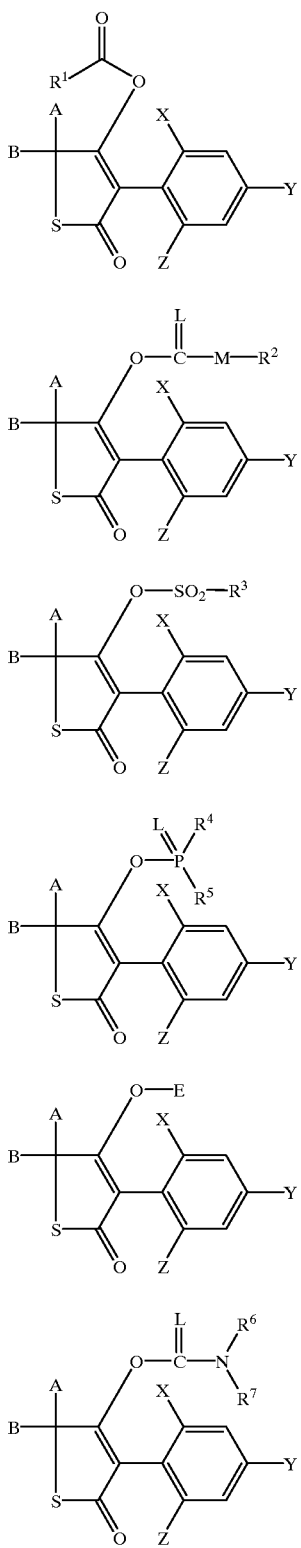

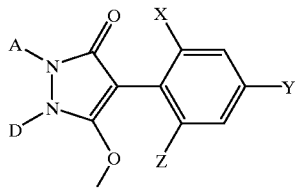

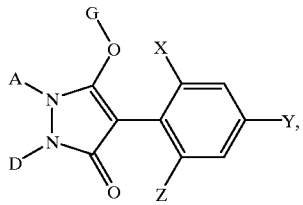

which is intended to be expressed by the broken line in formula (I-4).

The compounds of the formulae (I-4)$_a$ and (I-4)$_b$ can exist as mixtures and also in the form of their pure isomers, If appropriate, mixtures of the compounds of the formulae (I-4)$_a$ and (I-4)$_b$ can be separated in a manner known per se using physical methods, for example by chromatographic methods.

For reasons of improved clarity, the following text will always mention only one of the isomers which are possible. This does not exclude the fact that the compounds can be present, if appropriate, in the form of the isomer mixtures or in the respective other isomeric form.

Taking into consideration the various meanings (b), (c), (d), (e), (f) and (g) of group G, the following main structures (I-4-b) to (I-4-g) result if Het represents group (4).

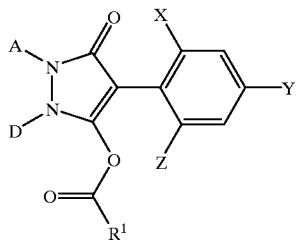

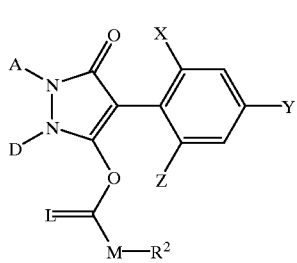

in which
A, B, E, L, M, X, Y, Z, R, $R^1$, $R^2$, $R^3$, $R^4$, $R^5$, $R^6$ and $R^7$ have the abovementioned meanings.

Depending on the position of the substituent G, the compounds of the formula (I-4) can exist in the two isomeric forms (I-4)$_a$ and (I-4)$_b$ -continued (I-4-d)
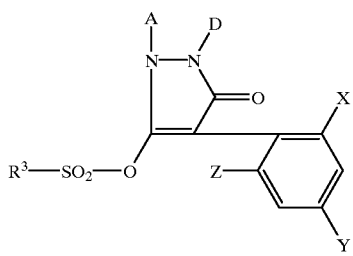

(I-4-e)
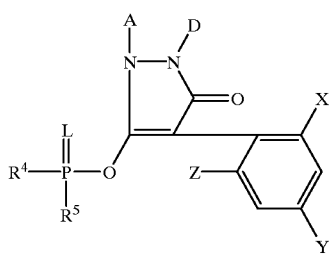

(I-4-f)
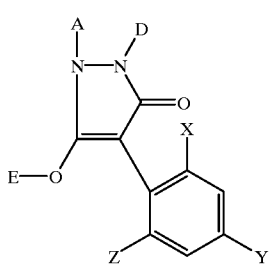

(I-4-g)
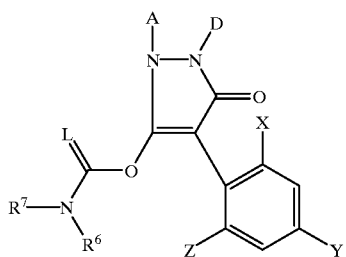

in which

A, D, E, L, M, X, Y, Z, $R^1$, $R^2$, $R^3$, $R^4$, $R^5$, $R^6$ and $R^7$ have the abovementioned meanings.

Depending on the position of the substituent G, the compounds of the formula (I-5) can exist in the two isomeric forms (I-5)$_a$ and (I-5)$_b$ (I-5)$_a$
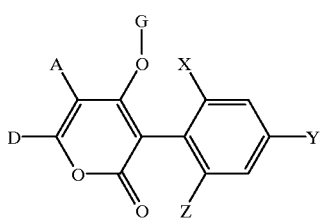

-continued (I-5)$_b$
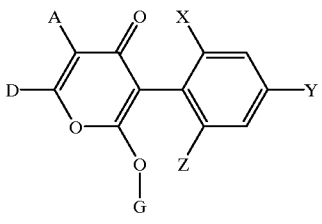

which is intended to be expressed by the broken line in formula (I-5).

The compounds of the formulae (I-5)$_a$ and (I-5)$_b$ can exist as mixtures and also in the form of their pure isomers. If appropriate, mixtures of the compounds of the formulae (I-5)$_a$ and (I-5)$_b$ can be separated in a manner known per se using physical methods, for example by chromatographic methods.

For reasons of improved clarity, the following text will always mention only one of the isomers which are possible. This does not exclude the fact that the compounds can be present, if appropriate, in the form of the isomer mixtures or in the respective other isomeric form.

Taking into consideration the various meanings (a), (b), (c), (d), (e), (f) and (g) of group G, the following main structures (I-5-a) to (I-5-b) result if Het represents group (5).

(I-5-a)
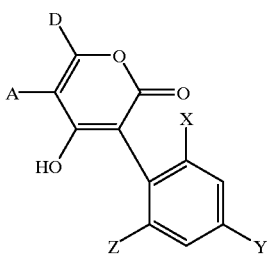

(I-5-b)
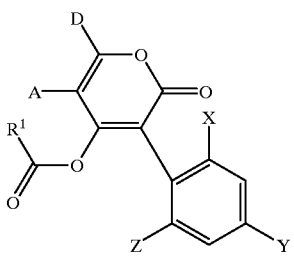

(I-5-c)
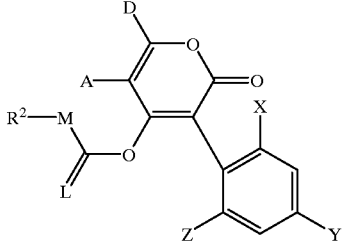

(I-5-d)
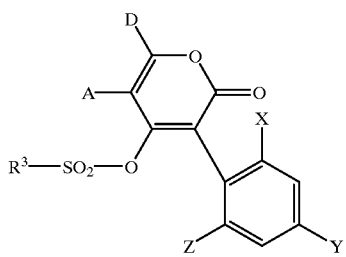
(I-5-e)
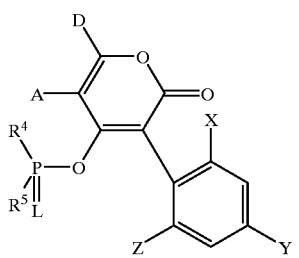
(I-5-f)
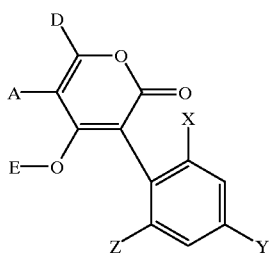
(I-5-g)
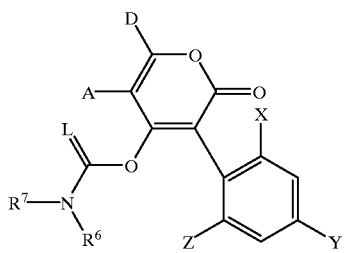
in which
A, D, E, L, M, X, Y, Z, $R^1$, $R^2$, $R^3$, $R^4$, $R^5$, $R^6$ and $R^7$ have the abovementioned meanings.
Taking into consideration the various meanings (a), (b), (c), (d), (e), (f) and (g) of group G, the following main structures (I-6-a) to (I-6-g) result if Het represents group (6)
(I-6-a)
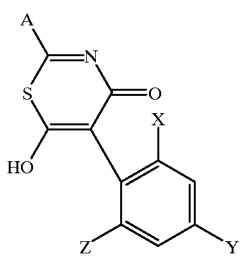
(I-6-b)
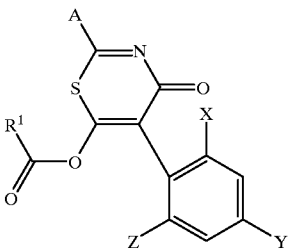
(I-6-c)
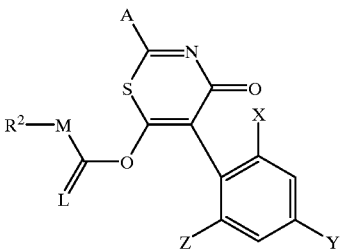
(I-6-d)
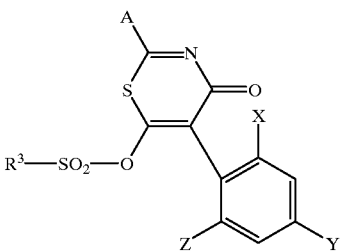
(I-6-e)
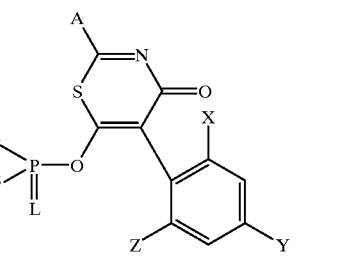
(I-6-f)
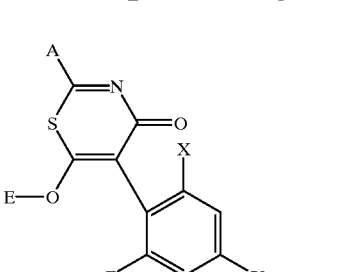
(I-6-g)
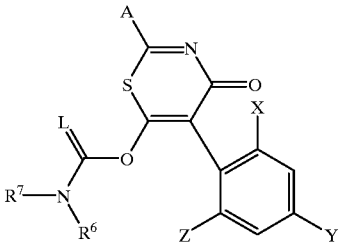

in which

A, E, L, M, X, Y, Z, $R^1$, $R^2$, $R^3$, $R^4$, $R^5$, $R^6$ and $R^7$ have the abovementioned meanings.

Furthermore, it has been found that the new compounds of the formula (I) are obtained by one of the processes described below:

(A) Substituted 3-phenylpyrrolidine-2,4-diones or their enols of the formula (I-1-a)

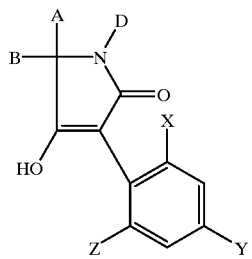

(I-1-a)

in which
A, B, D, X, Y and Z have the abovementioned meanings are obtained when

N-acylamino acid esters of the formula (II)

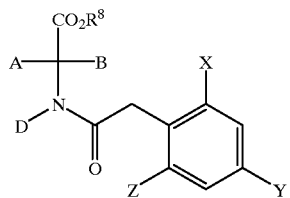

(II)

in which
A, B, D, X, Y and Z have the abovementioned meanings and
$R^8$ represents alkyl (preferably $C_1$–$C_6$-alkyl)

are subjected to an intramolecular condensation reaction in the presence of a diluent and in the presence of a base.

(B) Furthermore, it has been found that substituted 3-phenyl-4-hydroxy-$\Delta^3$-dihydrofuranone derivatives of the formula (I-2-a)

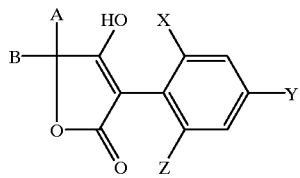

(I-2-a)

in which
A, B, X, Y and Z have the abovementioned meanings
are obtained when
carboxylic esters of the formula (III)

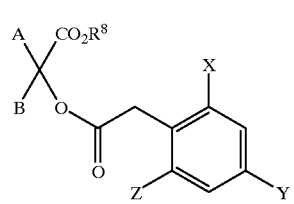

(III)

in which
A, B, X, Y, Z and $R^8$ have the abovementioned meanings are subjected to an intramolecular condensation reaction in the presence of a diluent and in the presence of a base.

(C) Furthermore, it has been found that substituted 3-phenyl-4-hydroxy-$\Delta^3$-dihydrothiophenone derivatives of the formula (I-3-a)

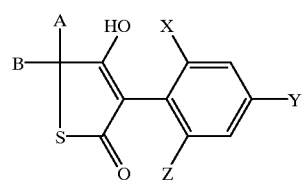

(I-3-a)

in which
A, B, X, Y and Z have the abovementioned meanings are obtained when

β-ketocarboxylic esters of the formula (IV)

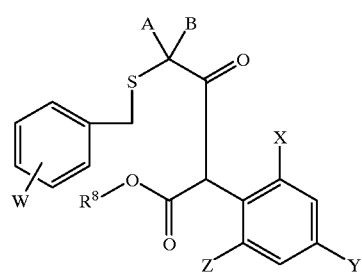

(IV)

in which
A, B, X, Y, Z and $R^8$ have the abovementioned meanings and
W represents hydrogen, halogen, alkyl (preferably $C_1$–$C_6$-alkyl) or alkoxy (preferably $C_1$–$C_8$-alkoxy)

are subjected to an intramolecular cyclization in the presence of a diluent and in the presence of an acid.

(E) Furthermore, it has been found that the new substituted 3-phenyl-pyrone derivatives of the formula (I-5-a)

(I-5-a)

in which
A, D, X, Y and Z have the abovementioned meanings
are obtained when
carbonyl compounds of the formula (VIII)

(VIII)

$$D-\overset{O}{\underset{\|}{C}}-CH_2-A$$

in which
A and D have the abovementioned meanings
or their silyl enol ethers of the formula (VIIIa)

(VIIIa)

$$D-\overset{CHA}{\underset{\|}{C}}-OSi(R^8)_3$$

in which
A, D and $R^8$ have the abovementioned meanings
are reacted with ketene acid halides of the formula (V)

(V)

in which
X, Y and Z have the abovementioned meanings and
Hal represents halogen (preferably chlorine or bromine),
if appropriate in the presence of a diluent and if appropriate in the presence of an acid acceptor.

(F) Furthermore, it has been found that the new substituted phenyl-1,3-thiazine derivatives of the formula (I-6-a)

(I-6-a)

in which
A, X, Y and Z have the abovementioned meanings
are obtained when thioamides of the formula (IX)

(IX)

$$H_2N-\overset{S}{\underset{\|}{C}}-A$$

in which
A has the abovementioned meaning
are reacted with ketene acid halides of the formula (V)

(V)

in which
Hal, X, Y and Z have the abovementioned meanings,
if appropriate in the presence of a diluent and if appropriate in the presence of an acid acceptor.

Furthermore, it has been found (G) that the compounds of the formulae (I-1-b) to (I-3-b), (I-5-b) and (I-6-b) shown above in which A, B, D, $R^1$, X, Y and Z have the abovementioned meanings are obtained when compounds of the formulae (I-1-a) to (I-3-a), (I-5-a) and (I-6-a) shown above in which A, B, D, X, Y and Z have the abovementioned meanings, and that compounds of the formula (I-4-b) shown above in which A, D, $R^1$, X, Y and Z have the abovementioned meanings are obtained when compounds of the formula (I-4-a)

(I-4-a)

in which
A, D, X, Y and Z have the abovementioned meanings
are reacted in each case
α) with acid halides of the formula (X)

(X)

in which
$R^1$ has the abovementioned meaning and
Hal represents halogen (in particular chlorine or bromine), or
β) with carboxylic anhydrides of the formula (XI)

$$R^1-CO-O-CO-R^1 \quad (XI)$$

in which

R¹ has the abovementioned meaning, if appropriate in the presence of a diluent and if appropriate in the presence of an acid-binding agent;

(H) that the compounds of the formulae (I-1-c) to (I-6-c) shown above in which A, B, D, R², M, X, Y and Z have the abovementioned meanings and L represents oxygen are obtained when compounds of the formulae (I-1-a) to (I-6-a) shown above in which A, B, D, X, Y and Z have the abovementioned meanings are reacted in each case with chloroformic esters or chloroformic thiol esters of the formula (XII)

R²—M—CO—Cl (XII)

in which

R² and M have the abovementioned meanings, if appropriate in the presence of a diluent and if appropriate in the presence of an acid-binding agent;

(I) that compounds of the formulae (I-1-c) to (I-6-c) shown above in which A, B, D, R², M, X, Y and Z have the abovementioned meanings and L represents sulphur are obtained when compounds of the formulae (I-1-a) to (I-6-a) shown above in which A, B, D, X, Y and Z have the abovementioned meanings are reacted in each case α) with chloromonothioformic esters or chlorodithioformic esters of the formula (XIII)

(XIII)

in which

M and R² have the abovementioned meanings, if appropriate in the presence of a diluent and if appropriate in the presence of an acid-binding agent, or β) with carbon disulphide and subsequently with alkyl halides of the formula (XIV)

R²—Hal (XIV)

in which

R² has the abovementioned meaning and

Hal represents chlorine, bromine or iodine, if appropriate in the presence of a diluent and in the presence of a base, (J) that compounds of the formulae (I-1-d) to (I-6-d) shown above in which A, B, D, R³, X, Y and Z have the abovementioned meanings are obtained when compounds of the formulae (I-1-a) to (I-6-a) shown above in which A, B, D, X, Y and Z have the abovementioned meanings are reacted in each case with sulphonyl chlorides of the formula (XV)

R³—SO₂—Cl (XV)

in which

R³ has the abovementioned meaning, if appropriate in the presence of a diluent and if appropriate in the presence of an acid-binding agent, (K) that compounds of the formulae (I-1-e) to (I-6-e) shown above in which A B, D, L, R⁴, R⁵, X, Y and Z have the abovementioned meanings are obtained when compounds of the formulae (I-1-a) to (I-6-a) shown above in which A, B, D, X, Y and Z have the abovementioned meanings are reacted in each case with phosphorus compounds of the formula (XVI)

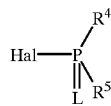

(XVI)

in which

L, R⁴ and R⁵ have the abovementioned meanings and

Hal represents halogen (in particular chlorine or bromine), if appropriate in the presence of a diluent and if appropriate in the presence of an acid-binding agent, (L) that compounds of the formulae (I-1-f) to (I-6-f) shown above in which A, B, D, E, X, Y and Z have the abovementioned meanings are obtained when compounds of the formulae (I-1-a) to (I-6-a) in which A, B, D, X, Y and Z have the abovementioned meanings are in each case reacted with metal compounds or amines of the formulae (XVII) or (XVIII)

Me(OR¹⁰)ₜ (XVII)

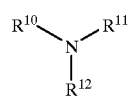

(XVIII)

in which

Me represents a mono- or divalent metal (preferably an alkali metal or alkaline earth metal, such as lithium, sodium, potassium, magnesium or calcium), t represents the number 1 or 2 and R¹⁰, R¹¹ and R¹² independently of one another represent hydrogen or alkyl (preferably C₁–C₈-alkyl), if appropriate in the presence of a diluent, (M) that compounds of the formulae (I-1-g) to (I-6-g) shown above in which A, B, D, L, R⁶, R⁷, X, Y and Z have the abovementioned meanings are obtained when compounds of the formulae (I-1-a) to (I-6-a) shown above in which A, B, D, X, Y and Z have the abovementioned meanings are reacted in each case α) with isocyanates or isothiocyanates of the formula (XIX)

R⁶—N=C=L (XIX)

in which

R⁶ and L have the abovementioned meanings, if appropriate in the presence of a diluent and if appropriate in the presence of a catalyst, or β) with carbamoyl chlorides or thiocarbamoyl chlorides of the formula (XX)

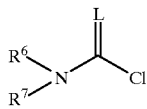
(XX)

in which

L, $R^6$ and $R^7$ have the abovementioned meanings, if appropriate in the presence of a diluent and if appropriate in the presence of an acid-binding agent.

The compounds according to the invention of the formulae (I-1-a), (I-2-a), (I-3-a), (I-5-a) and (I-6-a) are thus important intermediates for the preparation of the compounds according to the invention of the formulae (I-1), (I-2), (I-3), (I-4), (I-5) and (I-6) in which G represents in each case one of the groups b), c), d), e), f) or g).

Furthermore, it has been found that the new compounds of the formula (I) have a very good activity when used as pesticides, preferably as insecticides, acaricides and herbicides.

Formula (I) provides a general definition of the compounds according to the invention. Preferred substituents or ranges of the radicals given in the formulae mentioned hereinabove and hereinbelow are illustrated in the following text:

X preferably represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano, or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

Y preferably represents hydrogen, halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkyl-sulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano.

Z preferably represents hydrogen, halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano.

Het preferably represents one of the groups

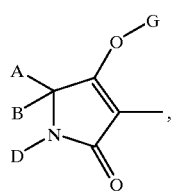
(1)

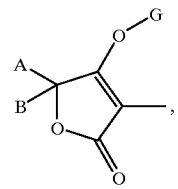
(2)

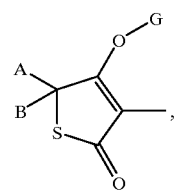
(3)

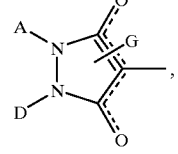
(4)

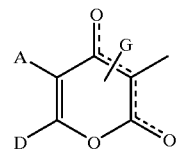
(5)

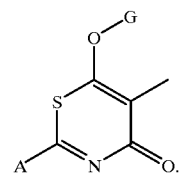
(6)

A preferably represents hydrogen, or represents $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or represents $C_3$–$C_8$-cycloalkyl in which up to two ring members are optionally replaced by oxygen and/or sulphur and which is optionally substituted by halogen, $C_1$–$C_6$-alkyl or $C_1$–$C_6$-alkoxy, or represents $C_6$- or $C_{10}$-aryl, hetaryl having 5 to 6 ring atoms or $C_6$- or $C_{10}$-aryl-$C_1$–$C_6$-alkyl, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro.

B preferably represents hydrogen, $C_1$–$C_{12}$-alkyl or $C_1$–$C_8$-alkoxy-$C_1$–$C_6$-alkyl, or A, B and the carbon atom to which they are bonded preferably represent saturated or unsaturated $C_3$–$C_{10}$-cycloalkyl in which one ring member is optionally replaced by oxygen or sulphur and which is optionally monosubstituted or polysubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or A, B and the carbon atom to which they are bonded preferably represent $C_3$–$C_6$-cycloalkyl which is substituted by an alkylenedlyl group which optionally contains one or two oxygen and/or sulphur atoms or by an alkylenedioxy or by an alkylenedithio group, this group together with the carbon atom to which it is bonded forming a further five- to eight-membered ring, or A, B and the carbon atom to which they are bonded preferably represent $C_3$–$C_8$-cycloalkyl or $C_5$–$C_8$-cycloalkenyl in which two substituents together with the carbon atoms to which they are bonded represent $C_3$–$C_6$-alkanediyl, $C_3$–$C_6$-alkenediyl or $C_4$–$C_6$-alkanedienediyl, in which one methylene group is optionally replaced by oxygen or sulphur and each of which is optionally substituted by $C_1$–$C_6$-alkyl, $C_1$–$C_6$-alkoxy or halogen, D preferably represents hydrogen, or represents $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by halogen, or represents $C_3$–$C_8$-cycloalkyl in which up to two ring members are optionally replaced by oxygen and/or sulphur and which is optionally substituted by halogen, $C_1$–$C_4$-alkyl, $C_1$–$C_4$-alkoxy or $C_1$–$C_4$-halogenoalkyl, or represents phenyl, hetaryl having 5 or 6 ring atoms, phenyl-$C_1$–$C_6$-alkyl or hetaryl-$C_1$–$C_6$-alkyl having 5 or 6 ring atoms, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent in each case optionally substituted $C_3$–$C_6$-alkanediyl or $C_3$–$C_6$-alkenediyl, suitable substituents in each case being:

halogen, hydroxyl, mercapto, or $C_1$–$C_{10}$-alkyl, $C_1$–$C_6$-alkoxy, $C_1$–$C_6$-alkylthio, $C_3$–$C_7$-cycloalkyl, phenyl or benzyloxy, each of which is optionally substituted by halogen; or a further $C_3$–$C_6$-alkanediyl group, $C_3$–$C_6$-alkenediyl group or a butadienyl group which is optionally substituted by $C_1$–$C_6$-alkyl or in which two adjacent substituents together with the carbon atoms to which they are bonded optionally form a further saturated or unsaturated cycle having 5 to 6 ring atoms which can contain oxygen or sulphur, or which optionally contains one of the following groups

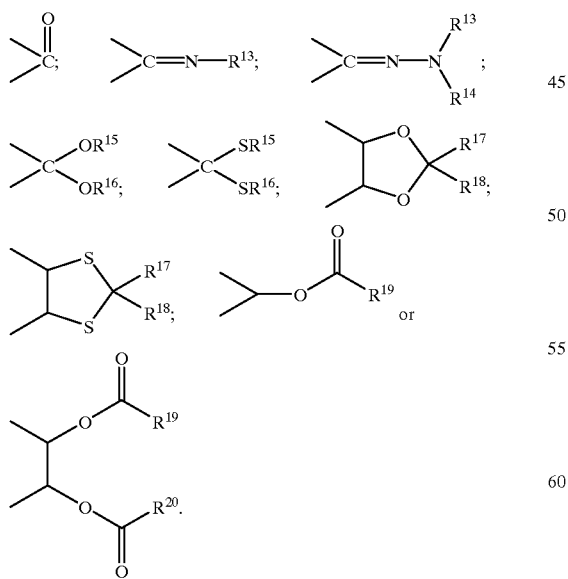

G, in the event that Het represents one of the radicals (1), (2), (3), (5) or (6), preferably represents hydrogen (a), or, in the event that Het represents one of the radicals (1), (2), (3), (4), (5) or (6), one of the groups

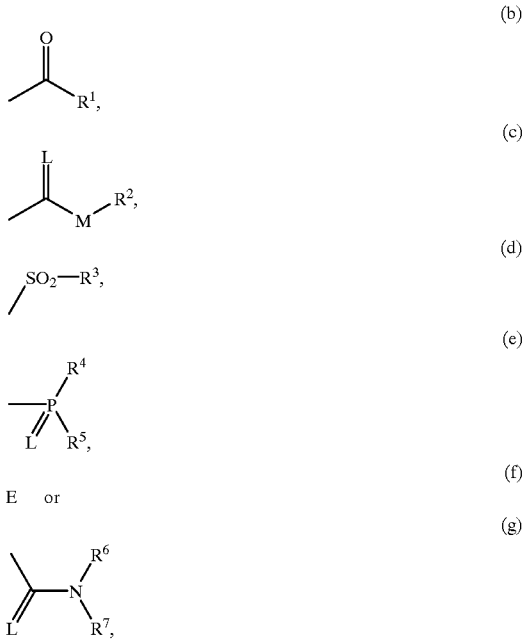

in which

E represents a metal ion equivalent or an ammonium ion,

L represents oxygen or sulphur and

M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents $C_3$–$C_8$-cycloalkyl in which at least one ring member is optionally replaced by oxygen and/or sulphur and which is optionally substituted by halogen, $C_1$–$C_6$-alkyl or $C_1$–$C_6$-alkoxy, or phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or 5- or 6-membered hetaryl which is optionally substituted by halogen or $C_1$–$C_6$-alkyl, or phenoxy-$C_1$–$C_6$-alkyl which is optionally substituted by halogen or $C_1$–$C_6$-alkyl, or 5- or 6-membered hetaryloxy-$C_1$–$C_6$-alkyl which is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, or $C_3$–$C_8$-cycloalkyl which is optionally substituted by halogen, $C_1$–$C_6$-alkyl $C_1$–$C_6$-alkoxy, or phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ preferably represents $C_1$–$C_8$-alkyl which is optionally substituted by halogen, or phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ preferably independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio or $C_3$–$C_7$-cycloalkylthio, each of which is optionally substituted by halogen, or phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, or phenyl which is optionally substituted by halogen, $C_1$–$C_8$-halogenoalkyl, $C_1$–$C_8$-alkyl or $C_1$–$C_8$-alkoxy, or benzyl which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical in which one carbon atom is optionally replaced by oxygen or sulphur.

$R^{13}$ preferably represents hydrogen, $C_1$–$C_8$-alkyl or $C_1$–$C_8$-alkoxy, each of which is optionally substituted by halogen, $C_3$–$C_8$-cycloalkyl in which one methylene group is optionally replaced by oxygen or sulphur and which is optionally substituted by halogen, $C_1$–$C_4$-alkyl or $C_1$–$C_4$-alkoxy, or phenyl, phenyl-$C_1$–$C_4$-alkyl or phenyl-$C_1$–$C_4$-alkoxy, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^{14}$ preferably represents hydrogen or $C_1$–$C_8$-alkyl, or $R^{13}$ and $R^{14}$ together preferably represent $C_4$–$C_6$-alkanediyl.

$R^{15}$ and $R^{16}$ are identical or different and preferably represent $C_1$–$C_6$-alkyl, or $R^{15}$ and $R^{16}$ together preferably represent a $C_2$–$C_4$-alkanediyl radical which is optionally substituted by $C_1$–$C_6$-alkyl, $C_1$–$C_6$-halogenoalkyl or by phenyl which is optionally substituted by halogen, $C_1$–$C_6$-alkyl, $C_1$–$C_4$-halogenoalkyl, $C_1$–$C_6$-alkoxy, $C_1$–$C_4$-halogenoalkoxy, nitro or cyano.

$R^{17}$ and $R^{18}$ independently of one another preferably represent hydrogen, $C_1$–$C_8$-alkyl which is optionally substituted by halogen, or phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or $R^{17}$ and $R^{18}$ together with the carbon atom to which they are bonded represent a carbonyl group or $C_5$–$C_7$-cycloalkyl in which one methylene group is optionally replaced by oxygen or sulphur and which is optionally substituted by halogen, $C_1$–$C_4$-alkyl or $C_1$–$C_4$-alkoxy.

$R^{19}$ and $R^{20}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

X particularly preferably represents fluorine, chlorine, bromine, $C_1$–$C_4$-alkyl, $C_2$–$C_4$-alkenyl, $C_2$–$C_4$-alkinyl, $C_1$–$C_4$-alkoxy, $C_3$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_3$–$C_4$-halogenoalkenyl, $C_1$–$C_4$-halogenoalkoxy, $C_3$–$C_4$-halogenoalkenyloxy, nitro or cyano, or phenyl, phenoxy, phenylthio, benzyloxy or benzylthio, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

Y particularly preferably represents hydrogen, fluorine, chlorine, bromine, $C_1$–$C_4$-alkyl, $C_2$–$C_4$-alkenyl, $C_2$–$C_4$-alkinyl, $C_1$–$C_4$-alkoxy, $C_3$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_3$–$C_4$-halogenoalkenyl, $C_1$–$C_4$-halogenoalkoxy, $C_3$–$C_4$-halogenoalkenyloxy, nitro or cyano.

Z particularly preferably represents hydrogen, fluorine, chlorine, bromine, $C_1$–$C_4$-alkyl, $C_2$–$C_4$-alkenyl, $C_2$–$C_4$-alkinyl, $C_1$–$C_4$-halogenoalkyl, $C_3$–$C_4$-halogenoalkenyl, $C_1$–$C_4$-alkoxy, $C_3$–$C_4$-alkenyloxy, $C_1$–$C_4$-halogenoalkoxy, $C_3$–$C_4$-halogenoalkenyloxy, nitro or cyano.

Het particularly preferably represents one of the groups

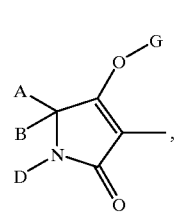

(1)

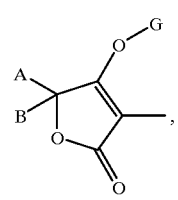

(2)

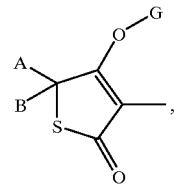

(3)

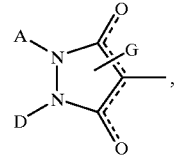

(4)

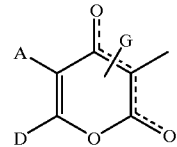

(5)

-continued (6)

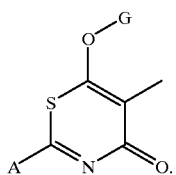

A particularly preferably represents hydrogen, or $C_1$–$C_{10}$-alkyl, $C_3$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or $C_3$–$C_7$-cycloalkyl in which up to two ring members are optionally replaced by oxygen and/or sulphur and which is optionally substituted by fluorine, chlorine, $C_1$–$C_4$-alkyl or $C_1$–$C_4$-alkoxy or phenyl, furanyl, pyridyl, imidazolyl, triazolyl, pyrazolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B particularly preferably represents hydrogen, $C_1$–$C_{10}$-alkyl or $C_1$–$C_6$-alkoxy-$C_1$–$C_4$-alkyl, or A, B and the carbon atom to which they are bonded particularly preferably represent saturated or unsaturated $C_3$–$C_8$-cycloalkyl in which one ring member is optionally replaced by oxygen or sulphur and which is optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are bonded particularly preferably represent $C_5$–$C_6$-cycloalkyl which is substituted by an alkylenediyl group which optionally contains one or two oxygen or sulphur atoms or by an alkylenedioxy or by an alkylenedithio group, this group together with the carbon atom to which it is bonded forming a further five- to seven-membered ring, or A, B and the carbon atom to which they are bonded particularly preferably represent $C_3$–$C_6$-cycloalkyl or $C_5$–$C_6$-cycloalkenyl, in which two substituents together with the carbon atoms to which they are bonded represent $C_3$–$C_5$-alkanediyl, $C_3$–$C_5$-alkenediyl or butadienediyl, in which one methylene group is optionally replaced by oxygen or sulphur and each of which is optionally substituted by $C_1$–$C_5$-alkyl, $C_1$–$C_5$-alkoxy, fluorine, chlorine or bromine.

D particularly preferably represents hydrogen, or $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, or $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl and in which one or two methylene groups which are not directly adjacent are optionally replaced by oxygen and/or sulphur, or phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together particularly preferably represent in each case optionally substituted $C_3$–$C_5$-alkanediyl or $C_3$–$C_5$-alkenediyl, suitable substituents in each case being:

fluorine, chlorine, hydroxyl, mercapto, or $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or which optionally contains one of the following groups:

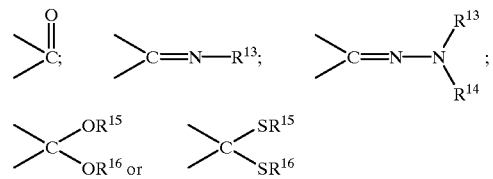

or A and D (in the case of the compounds of the formula (I-1)) together with the atoms to which they are bonded represent one of the groups AD-1 to AD-27

AD-1

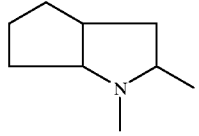

AD-2

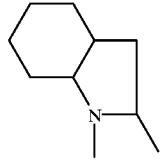

AD-3

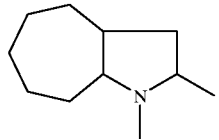

AD-4

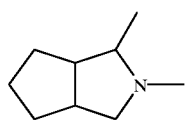

AD-5

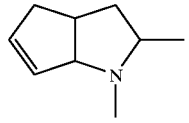

AD-6

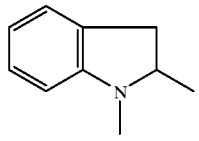

AD-7

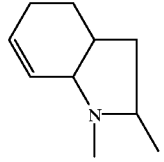

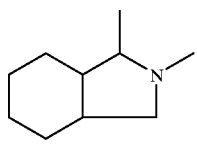
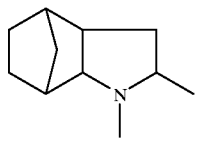
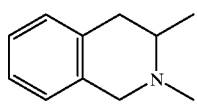
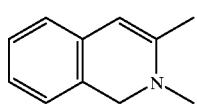
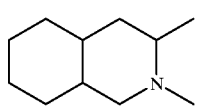
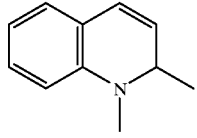
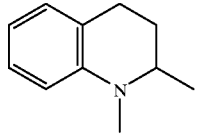
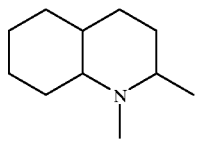
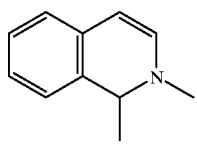
AD-8
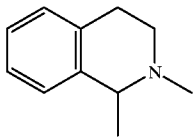
AD-9
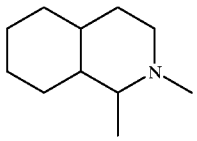
AD-10
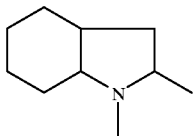
AD-11
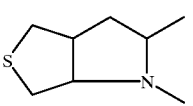
AD-12
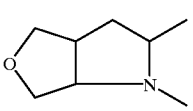
AD-13
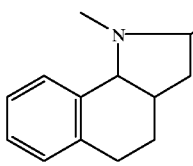
AD-14
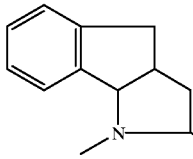
AD-15
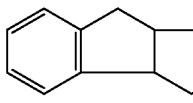
AD-16
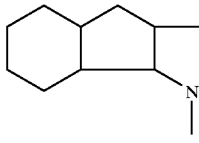
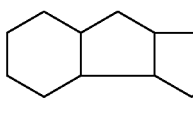
AD-17
AD-18
AD-19
AD-20
AD-21
AD-22
AD-23
AD-24
AD-25
AD-26

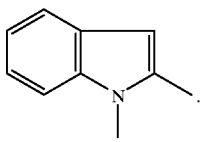

AD-27

G, in the event that Het represents one of the radicals (1), (2), (3), (5) or (6), particularly preferably represents hydrogen (a), or, in the event that Het represents one of the radicals (1), (2), (3), (4), (5) or (6), particularly preferably represents one of the groups

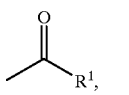 (b)

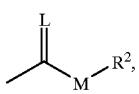 (c)

 (d)

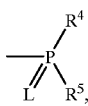 (e)

E (f)

or

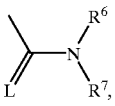 (g)

in which

E represents a metal ion equivalent or an ammonium ion,

L represents oxygen or sulphur and

M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or represents $C_3$–$C_7$-cycloalkyl which is optionally substituted by fluorine, chlorine, $C_1$–$C_5$-alkyl or $C_1$–$C_5$-alkoxy and in which up to two ring members are optionally replaced by oxygen and/or sulphur, or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, or phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, or pyrazolyl, thiazolyl, pyridyl, pyrimidyl, furanyl or thienyl, each of which is optionally substituted by fluorine, chlorine, bromine or $C_1$–$C_4$-alkyl, or phenoxy-$C_1$–$C_5$-alkyl which is optionally substituted by fluorine, chlorine, bromine or $C_1$–$C_4$-alkyl, or pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy, each of which is optionally substituted by fluorine or chlorine, or $C_3$–$C_7$-cycloalkyl which is optionally substituted by fluorine, chlorine, $C_1$–$C_4$-alkyl or $C_1$–$C_4$-alkoxy, or phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine, or phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro, $R^4$ and $R^5$ particularly preferably independently of one another represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio or $C_3$–$C_6$-cycloalkylthio, each of which is optionally substituted by fluorine or chlorine, or phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally substituted by halogen, or phenyl which is optionally substituted by halogen, $C_1$–$C_5$-halogenoalkyl, $C_1$–$C_5$-alkyl or $C_1$–$C_5$-alkoxy, or benzyl which is optionally substituted by halogen, $C_1$–$C_5$-alkyl, $C_1$–$C_5$-halogenoalkyl or $C_1$–$C_5$-alkoxy, or together represent a $C_3$–$C_6$-alkylene radical in which one carbon atom is optionally replaced by oxygen or sulphur.

$R^{13}$ particularly preferably represents hydrogen, or $C_1$–$C_6$-alkyl or $C_1$–$C_6$-alkoxy, each of which is optionally substituted by fluorine or chlorine, or $C_3$–$C_7$-cycloalkyl in which one methylene group is optionally replaced by oxygen or sulphur and which is optionally substituted by fluorine, $C_1$–$C_2$-alkyl or $C_1$–$C_2$-alkoxy, or phenyl, phenyl-$C_1$–$C_3$-alkyl or phenyl-$C_1$–$C_2$-alkyloxy, each of which is optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano.

$R^{14}$ particularly preferably represents hydrogen or $C_1$–$C_6$-alkyl, or $R^{13}$ and $R^{14}$ together particularly preferably represent $C_4$–$C_6$-alkanediyl.

$R^{15}$ and $R^{16}$ are identical or different and particularly preferably represent $C_1$–$C_4$-alkyl, or $R^{15}$ and $R^{16}$ together particularly preferably represent a $C_2$–$C_3$-alkanediyl radical which is optionally substituted by $C_1$–$C_4$-alkyl, $C_1$–$C_4$-haloalkyl or by phenyl which is optionally substituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, nitro or cyano.

X very particularly preferably represents fluorine, chlorine, bromine, methyl, ethyl, propyl, iso-propyl, vinyl, ethinyl, methoxy, ethoxy, propoxy, isopropoxy, allyloxy, methallyloxy, trifluoromethyl, difluoromethoxy, trifluoromethoxy, methylthio, methylsulphinyl, methylsulphonyl, nitro, cyano, or phenyl, phenoxy, phenylthio, benzyloxy or benzylthio, each of which is optionally substituted by fluorine, chlorine, bromine, methyl, ethyl, propyl, iso-propyl, tert-butyl, methoxy, ethoxy, propoxy, tert-butoxy, trifluoromethyl, trifluoromethoxy, nitro or cyano.

Y very particularly preferably represents hydrogen, fluorine, chlorine, bromine, methyl, ethyl, n-propyl, i-propyl, n-butyl, i-butyl, tert-butyl, vinyl, ethinyl, methoxy, ethoxy, propoxy, iso-propoxy, allyloxy, methallyloxy, trifluoromethyl, methylthio, methylsulphinyl, methylsulphonyl, difluoromethoxy, trifluoromethoxy, nitro or cyano.

Z very particularly preferably represents hydrogen, fluorine, chlorine, bromine, methyl, ethyl, n-propyl, i-propyl, n-butyl, i-butyl, tert-butyl, vinyl, ethinyl, methoxy, ethoxy, propoxy, iso-propoxy, allyloxy, methallyloxy, difluoromethoxy, trifluoromethyl, trifluoromethoxy, nitro or cyano.

Het very particularly preferably represents one of the groups

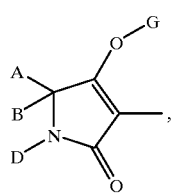

(1)

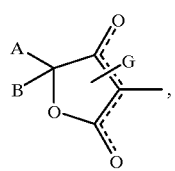

(2)

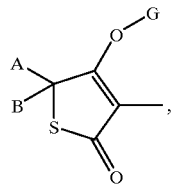

(3)

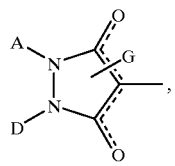

(4)

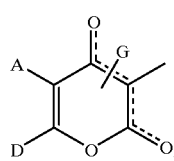

(5)

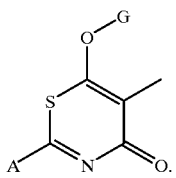

(6)

A very particularly preferably represents hydrogen, or $C_1$–$C_8$-alkyl, $C_3$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or $C_3$–$C_6$-cycloalkyl which is optionally substituted by fluorine, chlorine, methyl, ethyl or methoxy and in which up to two ring members are optionally replaced by oxygen and/or sulphur, or phenyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro.

B very particularly preferably represents hydrogen, $C_1$–$C_8$-alkyl or $C_1$–$C_4$-alkoxy-$C_1$–$C_2$-alkyl, or A, B and the carbon atom to which they are bonded very particularly preferably represent saturated or unsaturated $C_3$–$C_8$-cycloalkyl in which one ring member is optionally replaced by oxygen or sulphur and which is optionally substituted by methyl, ethyl, propyl, isopropyl, butyl, isobutyl, sec-butyl, tert-butyl, cyclopropyl, cyclohexyl, trifluoromethyl, methoxy, ethoxy, propoxy, iso-propoxy, butoxy, iso-butoxy, sec-butoxy, tert-butoxy, methylthio, ethylthio, fluorine, chlorine or phenyl, or A, B and the carbon atom to which they are bonded very particularly preferably represent $C_5$–$C_6$-cycloalkyl which is substituted by an alkylenedlyl group which optionally contains one oxygen or sulphur atom or by an alkylenedioxy group, this group together with the carbon atom to which it is bonded forming, a further five- to six-membered ring, or A, B and the carbon atom to which they are bonded very particularly preferably represent $C_3$–$C_6$-cycloalkyl or $C_5$–$C_6$-cycloalkenyl in which two substituents together with the carbon atoms to which they are bonded represent $C_3$–$C_4$-alkanediyl, $C_3$–$C_4$-alkenediyl or butadienediyl, in each of which one methylene group is optionally replaced by oxygen or sulphur.

D very particularly preferably represents hydrogen, or $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl, each of which is optionally substituted by fluorine or chlorine and in one or two methylene groups which are not directly adjacent to each other are optionally replaced by oxygen and/or sulphur, or phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together very particularly preferably represent in each case optionally substituted $C_3$–$C_4$-alkanediyl or $C_3$–$C_4$-alkenediyl, in which one carbon atom is optionally replaced by oxygen or sulphur and each of which is optionally substituted by fluorine, chlorine, hydroxyl, mercapto, or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or each of which optionally contains one of the following groups

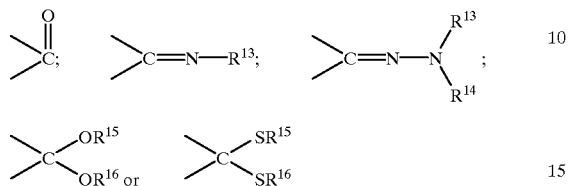

or A and D, in the case of the compounds of the formula (I-1), together with the atoms to which they are bonded, represent one of the following (groups:

AD-1

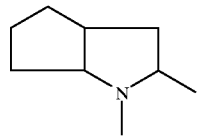

AD-2

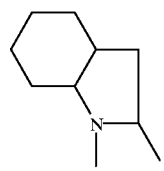

AD-4

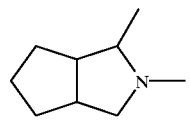

AD-6

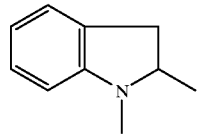

AD-8

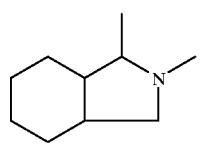

AD-10

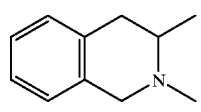

AD-12

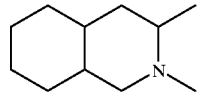

-continued

AD-14

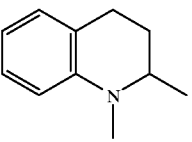

AD-15

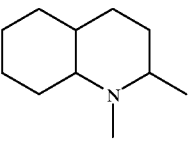

AD-17

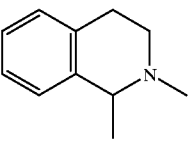

AD-18

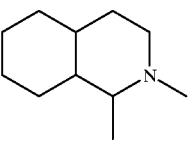

AD-27

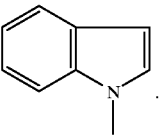

G, in the event that Het represents one of the radicals (1), (2), (3), (5) or (6), very particularly preferably represents hydrogen (a), or, in the event that Het represents one of the radicals (1), (2), (3), (4), (5) or (6), very particularly preferably represents one of the groups (b)

(c)

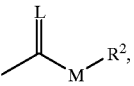

(d)

(e)

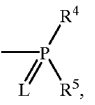

(f)

E or (g)

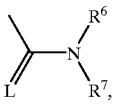

in which
- E represents a metal ion equivalent or an ammonium ion,
- L represents oxygen or sulphur and
- M represents oxygen or sulphur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally substituted by fluorine or chlorine, or $C_3$–$C_6$-cycloalkyl which is optionally substituted by fluorine, chlorine, methyl, ethyl, propyl, i-propyl, butyl, i-butyl, tert-butyl, methoxy, ethoxy, propoxy or iso-propoxy and in which up to two ring members are optionally replaced by oxygen and/or sulphur,
- or phenyl which is optionally substituted by fluorine, chlorine, bromine, cyano, nitro, methyl, ethyl, propyl, i-propyl, methoxy, ethoxy, trifluoromethyl, trifluoromethoxy, methylthio, ethylthio, methylsulphonyl or ethylsulphonyl,
- or benzyl which is optionally substituted by fluorine, chlorine, bromine, methyl, ethyl, propyl, i-propyl, methoxy, ethoxy, trifluoromethyl or trifluoromethoxy,
- or furanyl, thienyl, pyridyl, pyrimidyl, thiazolyl or pyrazolyl, each of which is optionally substituted by fluorine, chlorine, bromine, methyl or ethyl,
- or phenoxy-$C_1$–$C_4$-alkyl which is optionally substituted by fluorine, chlorine, methyl or ethyl, or pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_{14}$-alkyl, $C_2$–$C_{14}$-alkenyl, $C_1$–$C_4$-alkoxy-$C_2$–$C_6$-alkyl, poly-$C_1$–$C_4$-alkoxy-$C_2$–$C_6$-alkyl, each of which is optionally substituted by fluorine or chlorine,
- or $C_3$–$C_6$-cycloalkyl which is optionally substituted by fluorine, chlorine, methyl, ethyl, propyl, iso-propyl or methoxy,
- or phenyl or benzyl, each of which is optionally substituted by fluorine, chlorine, cyano, nitro, methyl, ethyl, propyl, i-propyl, methoxy, ethoxy, trifluoromethyl or trifluoromethoxy.

$R^3$ very particularly preferably represents methyl, ethyl, propyl or isopropyl, each of which is optionally substituted by fluorine or chlorine, or phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro, $R^4$ and $R^5$ very particularly preferably independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.

$R^6$ and $R^7$ independently of one another very particularly preferably represent hydrogen, or $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally substituted by fluorine or chlorine, or phenyl which is optionally substituted by fluorine, chlorine, bromine, $C_1$–$C_4$-halogenoalkyl, $C_1$–$C_4$-alkyl or $C_1$–$C_4$-alkoxy, or benzyl which is optionally substituted by fluorine, chlorine, bromine, $C_1$–$C_4$-alkyl, $C_1$–$C_4$-halogenoalkyl or $C_1$–$C_4$-alkoxy, or together represent a $C_5$–$C_6$-alkylene radical in which one carbon atom is optionally replaced by oxygen or sulphur.

$R^{13}$ very particularly preferably represents hydrogen, or $C_1$–$C_4$-alkyl or $C_1$–$C_4$-alkoxy, each of which is optionally substituted by fluorine or chlorine, or $C_3$–$C_6$-cycloalkyl, or phenyl, phenyl-$C_1$–$C_2$-alkyl or benzyloxy, each of which is optionally substituted by fluorine, chlorine, bromine, methyl, ethyl, iso-propyl, tert-butyl, methoxy, ethoxy, iso-propoxy, tert-butoxy, trifluoromethyl, trifluoromethoxy, nitro or cyano.

$R^{14}$ very particularly preferably represents hydrogen or $C_1$–$C_4$-alkyl, or $R^{13}$ and $R^{14}$ together ver particularly preferably represent $C_4$–$C_6$-alkanediyl.

$R^{15}$ and $R^{16}$ are identical or different and very particularly preferably represent methyl or ethyl, or $R^{15}$ and $R^{16}$ together very particularly preferably represent a $C_2$–$C_3$-alkanediyl radical which is optionally substituted by methyl, ethyl, n-propyl, iso-propyl, n-butyl, iso-butyl, sec-butyl, tert-butyl, or by phenyl which is optionally substituted by fluorine, chlorine, methoxy, trifluoromethyl, trifluoromethoxy, nitro or cyano.

The proviso is that in each case at least one of the substituents X and Y does not represent halogen, alkyl, halogenoalkyl or alkoxy.

The abovementioned definitions of radicals or illustrations, in general or where preferred ranges have been mentioned, can be combined with each other as desired, that is to say combinations between the respective ranges and preferred ranges are also possible. They apply to the end products and, analogously, to the precursors and intermediates.

Preferred according to the invention are the compounds of the formula (I) which contain a combination of the meanings mentioned above as being preferred (preferable).

Particularly preferred according to the invention are the compounds of the formula (I) which contain a combination of the meanings mentioned above as being particularly preferred.

Very particularly preferred according to the invention are the compounds of the formula (I) which contain a combination of the meanings mentioned above as being very particularly preferred.

Saturated or unsaturated hydrocarbon radicals, such as alkyl or alkenyl, also in connection with hetero atoms, such as, for example, in alkoxy, can be in each case straight-chain or branched as far as this is possible.

Optionally substituted radicals can be monosubstituted or polysubstituted, it being possible for the substituents to be identical or different in the case of the polysubstituted radicals.

Compounds of the formula (I-1-a) which may be mentioned individually in addition to the compounds mentioned in the preparation examples are those which follow:

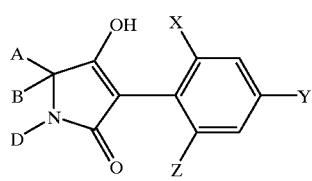

TABLE 1

X = CH₃, Y = CN, Z = CH₃

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |
| cyclopropyl | CH₃ | H |
| cyclopentyl | CH₃ | H |
| cyclohexyl | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHi-C₃H₇—(CH₂)₂— | | H |
| —(CH₂)₂—C(CH₃)₂—(CH₂)₂— | | H |
| —CH₂—(CHCH₃)₂—(CH₂)₂— | | H |
| —CH₂—CH—(CH₂)₂—CH—CH₂— (bridged) | | H |
| —CH₂—CH—(CH₂)₄—CH—CH₂— (bridged) | | H |

TABLE 1-continued

X = CH₃, Y = CN, Z = CH₃

| A | B | D |
|---|---|---|
| —CH₂—CH—(CH₂)₃—CH—(CH₂)₂— (bridged) | | H |
| indanyl (fused) | | H |
| tetrahydronaphthyl (fused) | | H |
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—S—CH₂— | | H |
| —CH₂—S—(CH₂)₂— | | H |
| —(CH₂)₂—S—CH₂— | | H |
| —CH₂—CH—(CH₂)₃—CH— (bridged) | | H |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |

Table 2: A, B and D as shown in Table 1
  X=C$_2$H$_5$; Y=CN; Z=CH$_3$
Table 3: A, B and D as shown in Table 1
  X=C$_2$H$_5$; Y=CN; Z=C$_2$H$_5$
Table 4: A, B and D as shown in Table 1
  X=CN; Y=CH$_3$; Z=CH$_3$
Table 5: A, B and D as shown in Table 1
  X=CN; Y=C$_2$H$_5$; Z=CH$_3$
Table 6: A, B and D as shown in Table 1
  X=CN; Y=C$_2$H$_5$; Z=C$_2$H$_5$
Table 7: A, B and D as shown in Table 1
  X=CN; Y=CH$_3$; Z=C$_2$H5
Table 8: A, B and D as shown in Table 1
  X=CN; Y=CH$_3$; Z=H
Table 9: A, B and D as shown in Table 1
  X=CH$_3$; Y=CN; Z=H
Table 10: A, B and D as shown in Table 1
  X=CN; Y=C$_2$H$_5$; Z=H
Table 11: A, B and D as shown in Table 1
  X=C$_2$H$_5$; Y=CN; Z=H
Table 12: A, B and D as shown in Table 1
  X=OCHF$_2$; Y=CH$_3$; Z=CH$_3$
Table 13: A, B and D as shown in Table 1
  X=O—CH$_2$CF$_3$; Y=CH$_3$; Z=CH$_3$
Table 14: A, B and D as shown in Table 1
  X=OCHF$_2$; Y=CH$_3$; Z=H
Table 15: A, B and D as shown in Table 1
  X=OCH$_2$CF$_3$; Y=CH$_3$; Z=H Compounds of the formula (I-2-a) which may be mentioned individually in addition to the compounds mentioned in the preparation examples are those which follow:

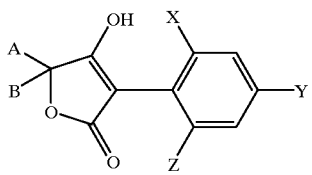

TABLE 16

| X = CH$_3$, Y = CN, Z = CH$_3$ | |
| --- | --- |
| A | B |
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |

TABLE 16-continued

| X = CH$_3$, Y = CN, Z = CH$_3$ | |
| --- | --- |
| A | B |
| △ (cyclopropyl) | CH$_3$ |
| cyclopentyl | CH$_3$ |
| cyclohexyl | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
| —CH$_2$—CH—(CH$_2$)$_2$—CH— with —CH$_2$— bridge | |
| —CH$_2$—CH————CH—CH$_2$— with —(CH$_2$)$_4$— bridge | |
| —CH$_2$—CH————CH—(CH$_2$)$_2$— with —(CH$_2$)$_3$— bridge | |
| indane | |
| tetrahydronaphthalene | |

Table 17: A and B as shown in Table 16
  X=C$_2$H$_5$; Y=CN; Z=CH$_3$
Table 18: A and B as shown in Table 16
  X=C$_2$H$_5$; Y=CN; Z=C$_2$H$_5$
Table 19: A and B as shown in Table 16
  X=CN; Y=CH$_3$; Z=CH$_3$
Table 20: A and B as shown in Table 16
  X=CN; Y=C$_2$H$_5$; Z=CH$_3$
Table 21: A and B as shown in Table 16
  X=CN; Y=C$_2$H$_5$; Z=C$_2$H$_5$
Table 22: A and B as shown in Table 16
  X=CN; Y=CH$_3$; Z=C$_2$H$_5$
Table 23: A and B as shown in Table 16

X=CN; Y=CH$_3$; Z=H

Table 24: A and B as shown in Table 16

X=CH$_3$; Y=CN; Z=H

Table 25: A and B as shown in Table 16

X=CN; Y=C$_2$H$_5$; Z=H

Table 26: A and B as shown in Table 16

X=C$_2$H$_5$; Y=CN; Z=H

Table 27: A and B as shown in Table 16

X=OCHF$_2$; Y=CH$_3$; Z=CH$_3$

Table 28: A and B as shown in Table 16

X=O—CH$_2$CF$_3$; Y=CH$_3$; Z=CH$_3$

Table 29: A and B as shown in Table 16

X=OCH$_2$CF$_3$; Y=CH$_3$; Z=H

Table 30: Y and B as shown in Table 16

X=OCH$_2$F; Y=CH$_3$; Z=H

If, in accordance with process (A), ethyl N-[(2-methylthio-4-methoxy)-phenylacetyl]-1-amino-4-ethyl-cyclohexane-carboxylate is used as startinc, material, the course of the process according to the invention can be represented by the following equation:

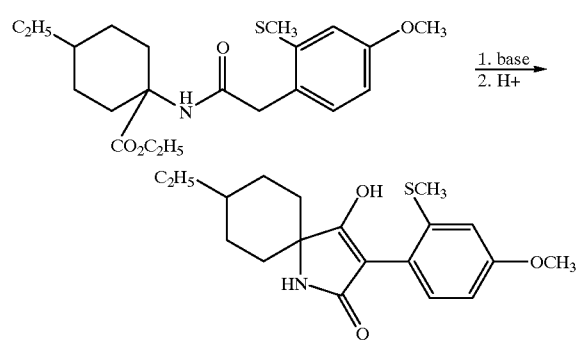

If, in accordance with process (B), ethyl O-[(2-chloro-4-sulphonylmethyl)-phenylacetyl]-hydroxyacetate is used, the course of the process according to the invention can be represented by the following equation:

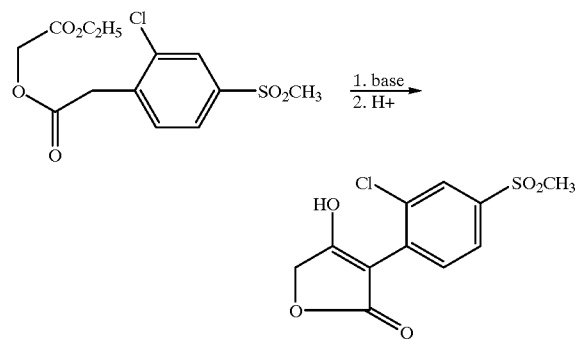

If, in accordance with process (C), ethyl 2-[(2-methoxy-4-sulphinylmethyl)-phenyl]-4-(4-methoxy)-benzylmercapto-4-methyl-3-oxo-valerate is used, the course of the process according to the invention can be represented by the following equation:

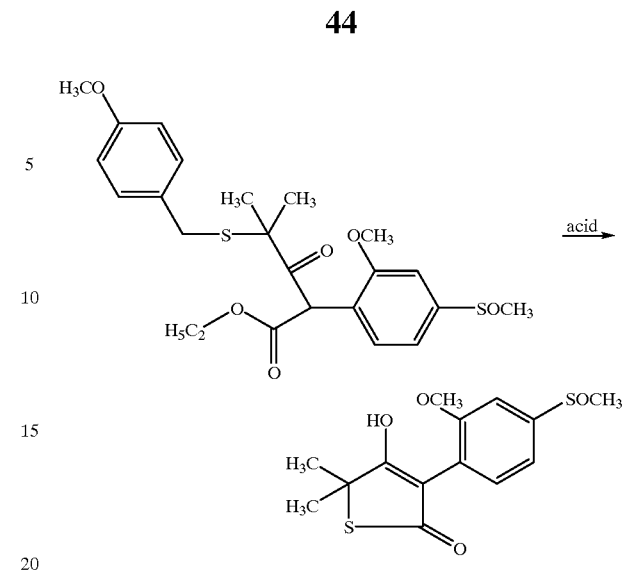

If, in accordance with process (E), for example (chlorocarbonyl)-2-[(2-methylthio-4-methoxy)-phenyl]-ketene and acetone are used as starting compounds, the course of the process according to the invention can be represented by the following equation:

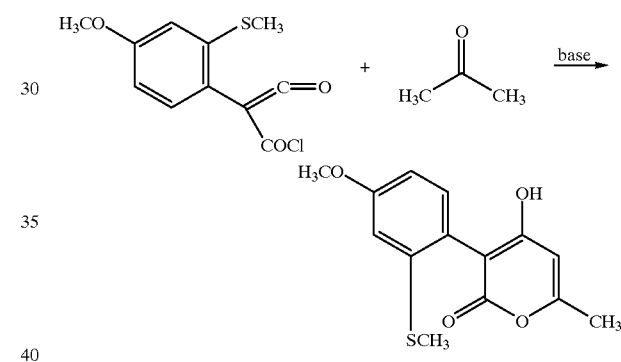

If, in accordance with process (F), for example (chlorocarbonyl)-2-[(2-methoxy-6-methylthio)-phenyl]-ketene and thiobenzamide are used as starting compounds, the course of the process according to the invention can be represented by the following equation:

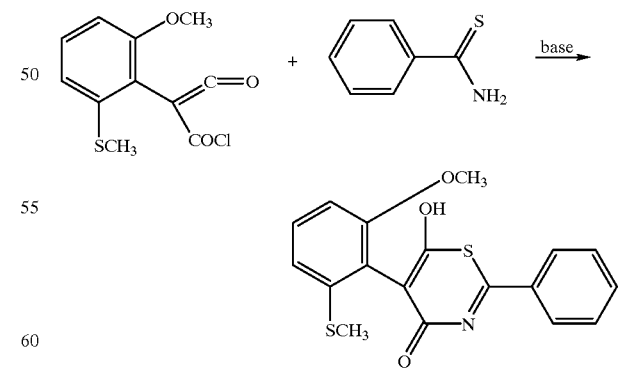

If, in accordance with process (Gα), 3-[(2-chloro-4-cyano)-phenyl]-5,5-dimethylpyrrolidine-2,4-dione and pivaloyl chloride are used as starting substances, the course of the process according to the invention can be represented by the following equation:

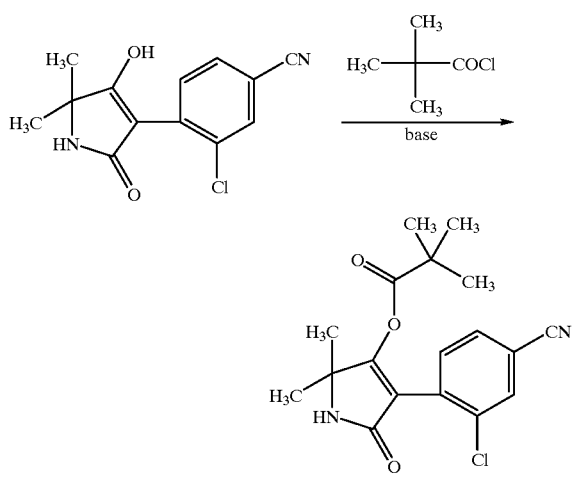

If, in accordance with process (G) (variant β), 3-[(4-chloro-2-cyano)-phenyl]-4-hydroxy-5-phenyl-Δ³-dihydrofuran-2-one and acetic anhydride are used as starting compounds, the course of the process according to the invention can be represented by the following equation:

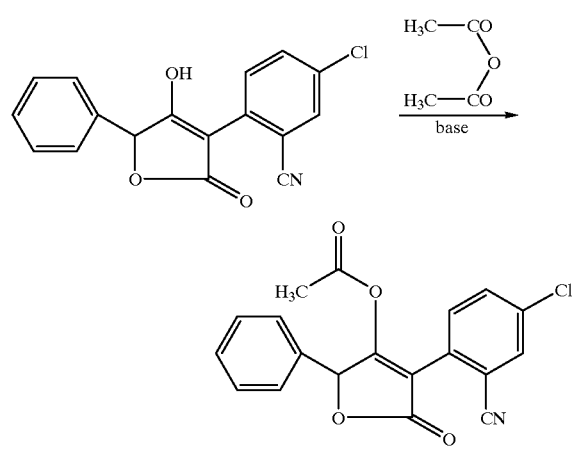

If, in accordance with process (H), 8-[(2,4-dicyano)-phenyl]-1,2-diaza-bicyclo-[4,3,0]-nonane-7,9-dione and ethoxyethyl chloroformate are used as starting compounds, the course of the process according to the invention can be represented by the following equation:

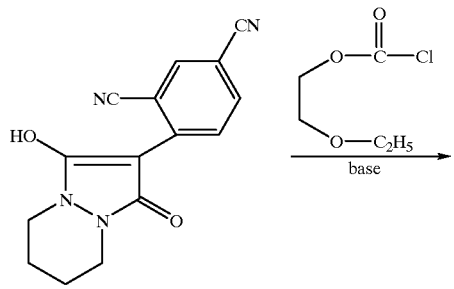

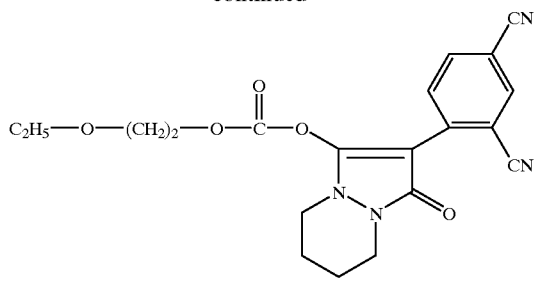

If, in accordance with process (I), variant α, 3-[(2-chloro-4-nitro)-phenyl]-4-hydroxy-6-(3-pyridyl)-pyrone and methyl chloromonothioformate are used as starting materials, the course of the reaction can be represented as follows:

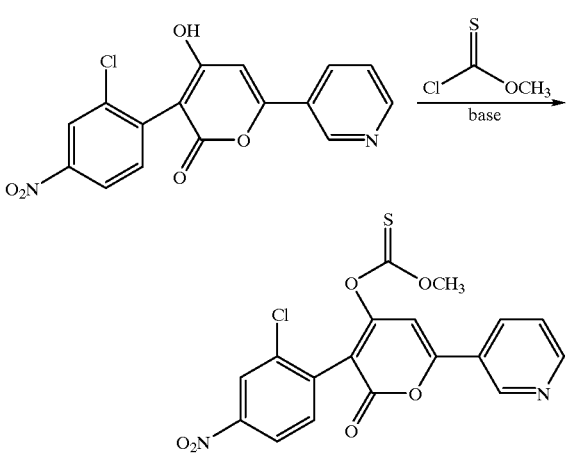

If, in accordance with process (K), variant β, 5-[(2-cyano-4-chloro)-phenyl]-6-hydroxy-2-(4-chlorophenyl)-thiazin-4-one, carbon disulphide and methyl iodide are used as starting components, the course of the reaction can be represented as follows:

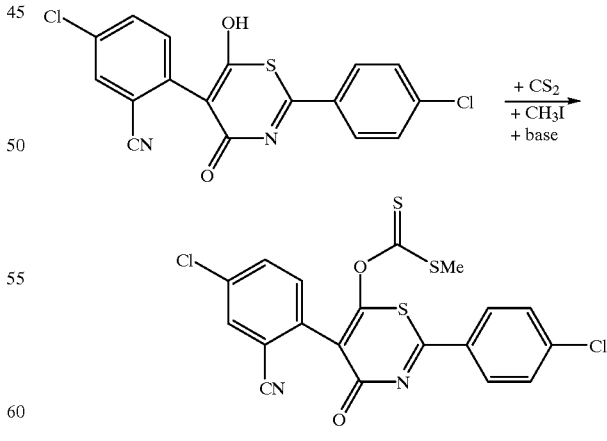

If, in accordance with process (J), 2-[(2-chloro-4-sulphonylmethyl)-phenyl]-3-hydroxy-4,4-(3-methoxy)-pentamethylene-Δ³-dihydrofuran-2-one and methanesulphonyl chloride are used as starting materials, the course of the reaction can be represented by the following equation:

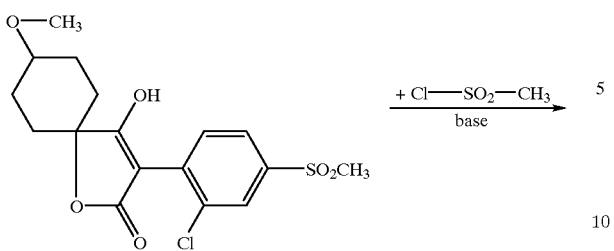

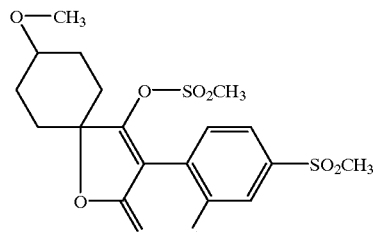

If, in accordance with process (K), 2-[(2-chloro-4-cyano)-phenyl]-3-hydroxy-5,5-dimethyl-Δ²-pyrrolidine-2,4-dione and 2,2,2-trifluoroethyl methylchlorothiophosphonate are used as starting materials, the course of the reaction can be represented by the following equation:

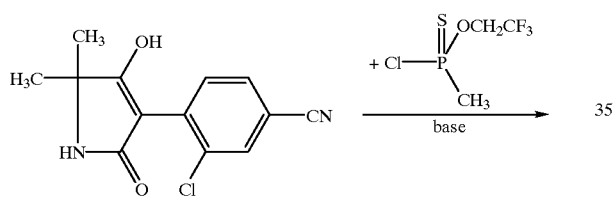

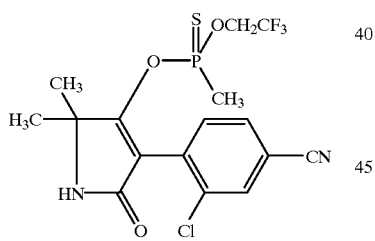

If, in accordance with process (L), 3-[(2,4-dicyano)-phenyl]-5-cyclopropyl-5-methyl-pyrrolidine-2,4-dione and NaOH are used as components, the course of the process according to the invention can be represented by the following equation:

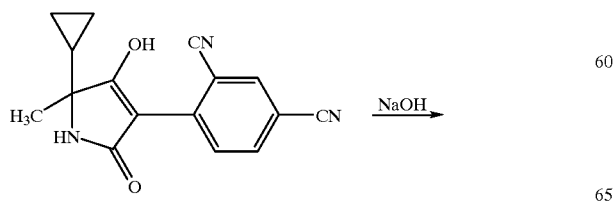

-continued

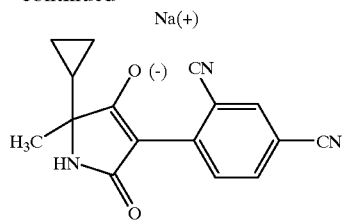

If, in accordance with process (M), variant α, 3-[(2-methylthio-4-methoxy)-phenyl]-4-hydroxy-5-tetramethylene-Δ³-dihydro-furan-2-one and ethyl isocyanate are used as starting materials, the course of the reaction can be represented by the following equation:

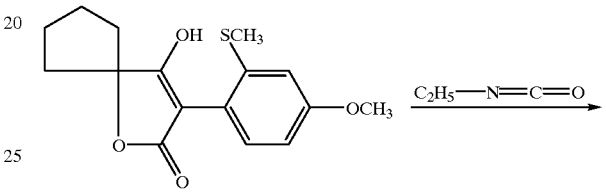

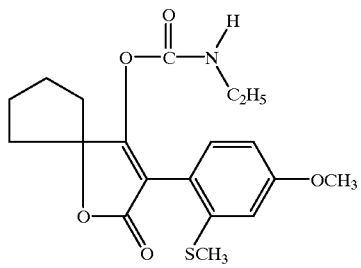

If, in accordance with process (M), variant β, 3-[(2-chloro-4-cyano)-phenyl]-5-methyl-pyrrolidine-2,4-dione and dimethylcarbamoyl chloride are used as starting materials, the course of the reaction can be represented by the following equation:

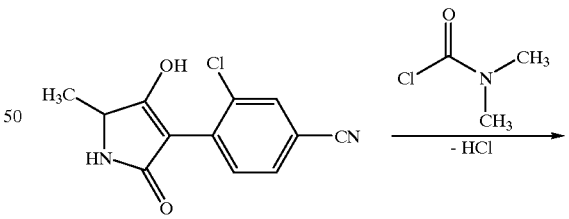

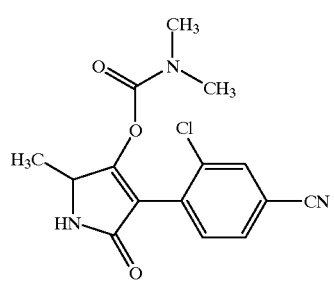

The compounds of the formula (II)

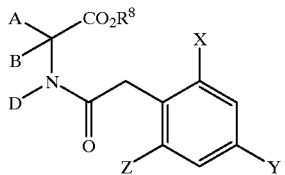
(II)

in which

A, B, D, X, Y, Z and R⁸ have the abovementioned meanings and which are required as starting materials in process (A) according to the invention are new.

The acylamino acid esters of the formula (II) are obtained, for example, when amino acid derivatives of the formula (XXI)

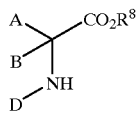
(XXI)

in which

A, B, R⁸ and D have the abovementioned meanings are acylated with substituted phenylacetyl halides of the formula (XXII)

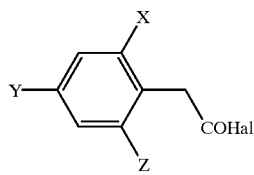
(XXII)

in which

X, Y and Z have the abovementioned meanings and

Hal represents chlorine or bromine (Chem. Reviews 52, 237–416 (1953); Bhattacharya, Indian J. Chem. 6, 341–5, 1968)

or when acylamino acids of the formula (XXIII)

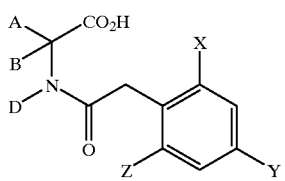
(XXIII)

in which

A, B, D, X, Y and Z have the abovementioned meanings are esterified (Chem. Ind. (London) 1568 (1968)).

The compounds of the formula (XXIII)

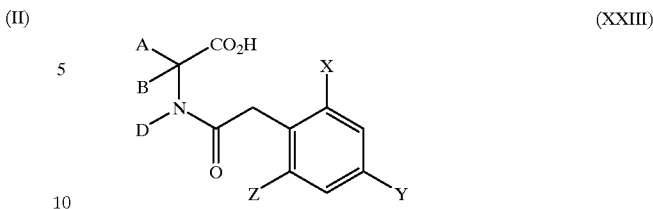
(XXIII)

in which

A,B,D,X,Y and Z have the abovementioned meanings are new.

The compounds of the formula (XXIII) are obtained when amino acids of the formula (XXIV)

(XXIV)

in which

A, B and D have the abovementioned meanings are acylated with substituted phenylacetyl halides of the formula (XXII)

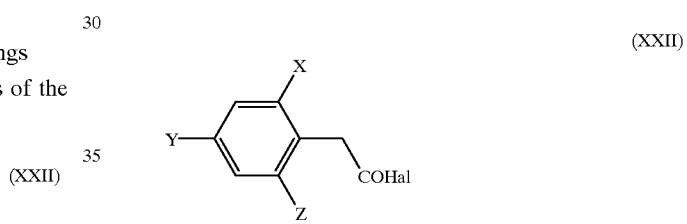
(XXII)

in which

X, Y and Z have the abovementioned meanings and

Hal represents chlorine or bromine in a Schotten-Baumann reaction (Organikum [Laboratory Practical in Organic Chemistry], VEB Deutscher Verlag der Wissenschaften, Berlin 1977, p. 505).

Some of the compounds of the formula (XXII) are known or can be prepared by known processes (see, for example, H. Henecka, Houben-Weyl, Methoden der Organischen Chemie [Methods in Organic Chemistry], Vol. 8, p. 467–469 (1952)).

Compounds of the formula (XXII-a)

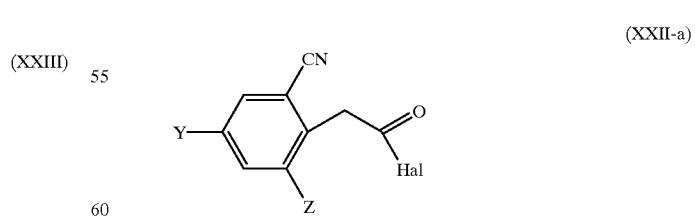
(XXII-a)

in which

Hal represents chlorine or bromine and

Y and Z have the abovementioned meanings, but do not simultaneously represent hydrogen, are new.

The compounds of the formula (XXII-a) are obtained, for example, by reacting substituted phenylacetic acids of the formula (XXVIII-a)

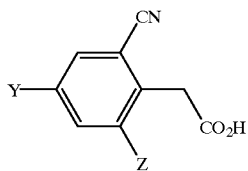
(XXVIII-a)

in which

Y and Z have the abovementioned meanings with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons, such as toluene or methylene chloride), at temperatures from −20° C. to 150° C., preferably from −10° C. to 100° C.

The compounds of the formula (XXVIII-a) are new.

The compounds of the formula (XXVIII-a) are obtained, for example, by hydrolysing substituted phenylacetic esters of the formula (XXX-a)

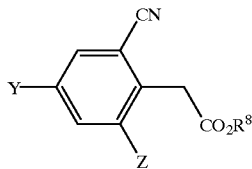
(XXX-a)

in which

Y, Z and $R^8$ have the abovementioned meanings in the presence of an acid (for example an inorganic acid, such as hydrochloric acid) or of a base (for example an alkali metal hydroxide, such as sodium hydroxide or potassium hydroxide) and, if appropriate, of a diluent (for example an aqueous alcohol, such as methanol or ethanol) at temperatures between 0° C. and 150° C., preferably between 20° C. and 100° C.

The compounds of the formula (XXX-a) are new.

Compounds of the formula (XXX-a)

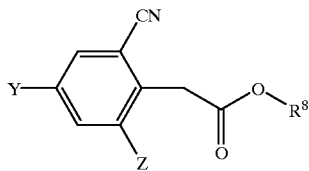
(XXX-a)

in which

Y, Z and $R^8$ have the abovementioned meanings are obtained when ortho-halophenylacetic esters of the formula (XXXIII-a)

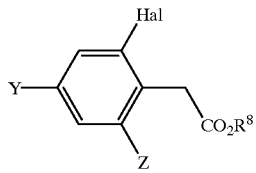
(XXXIII-a)

in which

Y, Z and $R^8$ have the abovementioned meanings and

Hal represents chlorine, bromine or iodine, in particular bromine, are reacted with copper cyanide in the presence of a diluent, such as, for example, dimethylformamide, dimethyl sulphoxide, N-methylpyrrolidone or sulpholane at temperatures from 50° C. to 250° C., preferably at 80° C. to 200° C.

The compounds of the formula (XXXIII) in which Y and Z represent alkyl are the subject-matter of the German patent application of the applicant with the file number 19523850.8 dated 30/06/1995.

Compounds of the formula (XXII-b)

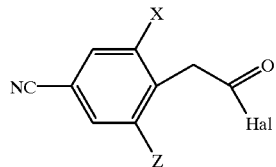
(XXII-b)

in which

Hal represents chlorine or bromine and

X and Z have the abovementioned meanings are new.

The compounds of the formula (XXII-b) are obtained, for example, by reacting substituted phenylacetic acids of the formula (XXVIII-b)

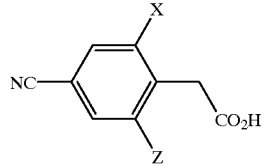
(XXVIII-b)

in which

X and Z have the abovementioned meanings with halogenating agents (for example thionyl chloride, thionyl bromide, oxalyl chloride, phosgene, phosphorus trichloride, phosphorus tribromide or phosphorus pentachloride) if appropriate in the presence of a diluent (for example optionally chlorinated aliphatic or aromatic hydrocarbons, such as toluene or methylene chloride) at temperatures from −20° C. to 150° C., preferably from −10° C. to 100° C.

The compounds of the formula (XXVIII-b) are new.

The compounds of the formula (XXVIII-b) are obtained, for example, by hydrolyzing substituted phenylacetic esters of the formula (XXX-b)

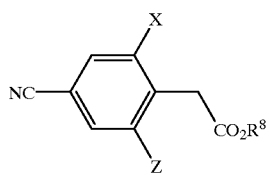

(XXX-b)

in which

X, Z and $R^8$ have the abovementioned meanings in the presence of an acid (for example an inorganic acid, such as hydrochloric acid) or of a base (for example an alkali metal hydroxide, such as sodium hydroxide or potassium hydroxide) and, if appropriate, of a diluent (for example an aqueous alcohol, such as methanol or ethanol) at temperatures between 0° C. and 150° C., preferably between 20° C. and 100° C.

The compounds of the formula (XXX-b) are new.

Compounds of the formula (XXX-b)

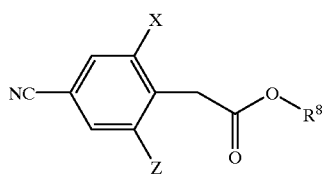

(XXX-b)

in which

X, Z and $R^8$ have the abovementioned meanings are obtained when para-halogenophenylacetic esters of the formula (XXXIII-b)

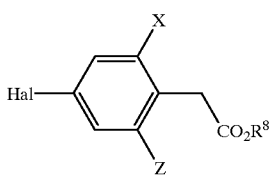

(XXXIII-b)

in which

X, Z and $R^8$ have the abovementioned meanings and

Hal represents chlorine, bromine or iodine, in particular bromine, are reacted with copper cyanide at temperatures from 50° C. to 250° C., preferably at 80° C. to 200° C., in the presence of a diluent, such as, for example, dimethylformamide, dimethyl sulphoxide, N-methylpyrrolidone or sulpholane.

The compounds of the formula (XXXIII-b) in which X and Z represent alkyl are the subject-matter of the German patent application of the applicant with the file number 19523850.8 dated 30/06/1995.

Compounds of the formula (XXII-c)

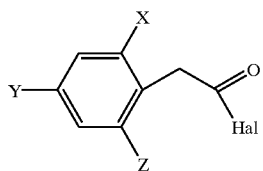

(XXII-c)

in which

Hal represents chlorine or bromine,

X represent $OCHF_2$ or $OCH_2CF_3$ and

Y and Z have the abovementioned meanings, but do not simultaneously represent hydrogen, are new.

The compounds of the formula (XXII-c) are obtained, for example, by reacting substituted phenylacetic acids of the formula (XXVIII-c)

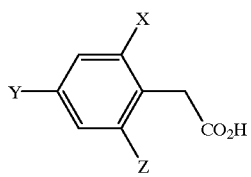

(XXVIII-c)

in which

X represents $OCHF_2$ or $OCH_2CF_3$ and

Y and Z have the abovementioned meanings with halogenating agents (for example thionyl chloride, thionyl bromide, oxalyl chloride, phosgene, phosphorus trichloride, phosphorus tribromide or phosphorus pentachloride) if appropriate in the presence of a diluent (for example optionally chlorinated aliphatic or aromatic hydrocarbons, such as toluene or methylene chloride) at temperatures from −20° C. to 150° C., preferably from −10° C. to 100° C.

The compounds of the formula (XXVIII-c) are new.

The compounds of the formula (XXVIII-c)

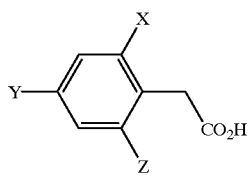

(XXVIII-c)

in which

X represents $OCHF_2$ or $OCH_2CF_3$ and

Y and Z have the abovementioned meanings are obtained when phenylacetaldehydes of the formula (XXXIV-c)

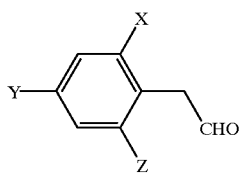

(XXXIV-c)

in which

X represents OCHF$_2$ or OCH$_2$CF$_3$ and

Y and Z have the abovementioned meanings are reacted in the presence of an oxidant, for example sodium chromate, sodium chlorite or oxygen, in the presence of a catalyst, in the presence of a diluent and, if appropriate, in the presence of a buffer at −50° C. to 150° C., preferably at 0° C. to 100° C.

The compounds of the formula (XXXIV-c) are new.

Phenylacetaldehydes of the formula (XXXIV-c)

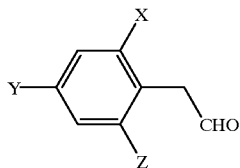

(XXXIV-c)

in which

X represents OCHF$_2$ or OCH$_2$CF$_3$ and

Y and Z have the abovementioned meanings are obtained when (2-propenyl)-phenyl ethers of the formula (XXXV-c)

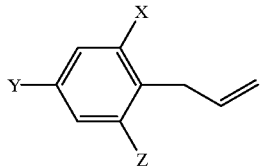

(XXXV-c)

in which

X represents OCHF$_2$ or OCH$_2$CF$_3$ and

Y and Z have the abovementioned meanings are reacted in the presence of ozone, in a solvent, for example dichloromethane, at −120° C. to 0° C., preferably at −80° C. to −20° C., and the product obtained is reduced using a reducing agent, for example dimethyl sulphide.

The compounds of the formula (XXXV-c) are new, but can be synthesized in a simple manner from the phenols by fragmentation by processes known in principle, for example as described by Rico J., Wakselman, C., J. Fluorine Chem. 20 765–70 (1982), or by nucleophilic substitution on phenolates, for example as described by Crossland, Wells, Shiner, J. Am. Chem. Soc. 93 4217 (1971).

Some of the compounds of the formulae (XXI) and (XXIV) are known and/or can be synthesized by known processes (see, for example, Compagnon, Miocque Ann. Chim. (Paris) [14] 5, p. 11–22, 23–27 (1970)).

The substituted cyclic amino carboxylic acids of the formula (XXIVa) in which A and B form a ring are generally obtained by means of a Bucherer-Bergs synthesis or a Strecker synthesis, where they are obtained in each case in various isomeric forms. Thus, the conditions of the Bucherer-Bergs synthesis preferentially give the isomers (for simplicity's sake termed β hereinbelow) in which the radicals R and the carboxyl group are in the equatorial position, while the conditions of the Strecker synthesis preferentially give the isomers (for simplicity's sake termed α hereinbelow) where the amino group and the radicals R are in the equatorial position.

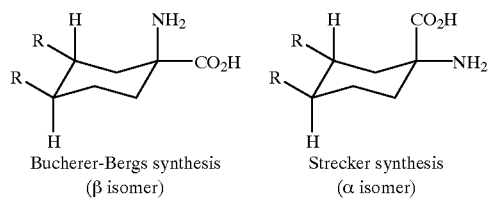

Bucherer-Bergs synthesis (β isomer)     Strecker synthesis (α isomer)

(L. Munday, J. Chem. Soc. 4372 (1961); J. T. Eward, C. Jitrangeri, Can. J. Chem. 53, 3339 (1975).

Furthermore, the starting substances of the formula (II)

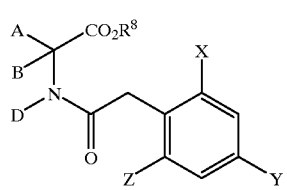

(II)

where

A, B, D, X, Y, Z and R$^8$ have the abovementioned meanings and which are used in the above process (A)

can be prepared when amino nitriles of the formula (XXV)

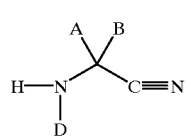

(XXV)

in which

A, B and D have the abovementioned meanings are reacted with substituted phenylacetyl halides of the formula (XXII)

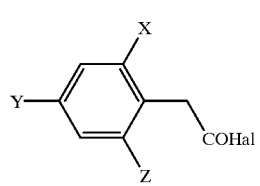

(XXII)

in which

X, Y, Z and Hal have the abovementioned meanings to give compounds of the formula (XXVI)

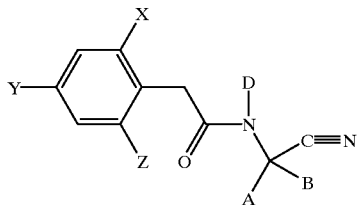

(XXVI)

in which

A, B, D, X, Y and Z have the abovementioned meanings and these are subsequently subjected to alcoholysis under acidic conditions.

The compounds of the formula (XXVI) are also new.

The compounds of the formula (III)

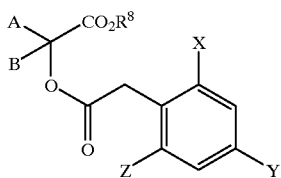

(III)

in which

A, B, X, Y, Z and $R^8$ have the abovementioned meanings and which are required as starting substances in process (B) according to the invention are new.

They can be prepared in a simple manner by methods known in principle.

Thus, O-acyl-α-hydroxy carboxylic esters of the formula (III) are obtained, for example, when 2-hydroxy carboxylic esters of the formula (XXVII)

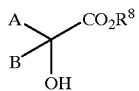

(XXVII)

in which

A, B and $R^8$ have the abovementioned meanings are acylated with substituted phenylacetyl halides of the formula (XXII)

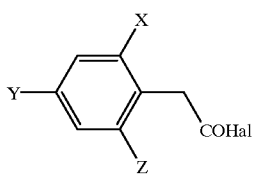

(XXII)

in which

X, Y, Z and Hal have the abovementioned meanings (Chem. Reviews 52, 237–416 (1953)).

Furthermore, compounds of the formula (III) are obtained when substituted phenylacetic acids of the formula (XXVIII)

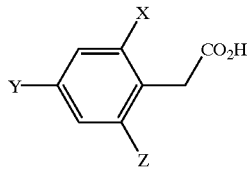

(XXVIII)

in which

X, Y and Z have the abovementioned meanings are alkylated with α-halogeno carboxylic esters of the formula (XXIX)

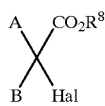

(XXIX)

in which

A, B and $R^8$ have the abovementioned meanings and

Hal represents chlorine or bromine.

Some of the compounds of the formula (XXVIII) are known and/or can be prepared in a simple manner by known processes, for example by hydrolysing phenylacetonitriles in the presence of acids or bases or by reducing mandelic esters or phenylglyoxylic acids with hydrogen (cf. Kindler et al., Chem. Ber. 76, 308, 1943). The compounds of the formula (XXIX) are commercially available.

The compounds of the formula (IV)

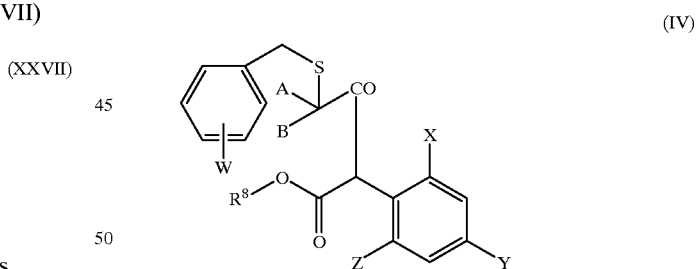

(IV)

in which

A, B, W, X, Y, Z and $R^8$ have the abovementioned meanings and which are required as starting substances in the above process (C)

are new.

They can be prepared by methods known in principle.

The compounds of the formula (IV) are obtained, for example, when substituted phenylacetic esters of the formula (XXX)

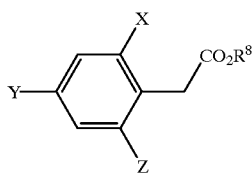

(XXX)

in which
X, Y, R$^8$ and Z have the abovementioned meanings
are acylated with 2-benzylthio-carboxylic halides of the formula (XXXI)

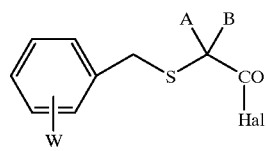

(XXXI)

in which
A, B and W have the abovementioned meanings and
Hal represents halogen (in particular chlorine or bromine) in the presence of strong bases (see, for example, M. S. Chambers, E. J. Thomas, D. J. Williams, J. Chem. Soc. Chem. Commun., (1987), 1228).

Some of the compounds of the formula (XXX) are new. Compounds of the formula (XXX) are obtained, for example, when compounds of the formula (XXVIII)

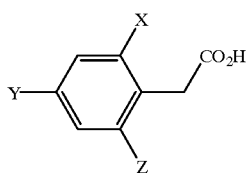

(XXVIII)

in which
X, Y and Z have the abovementioned meanings
are esterified in the presence of alcohols and dehydrating agents (for example conc. sulphuric acid)
or when alcohols are acylated with compounds of the formula (XXII)

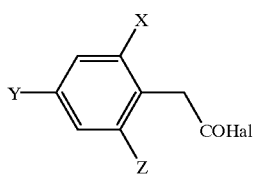

(XXII)

in which
X, Y, Z and Hal have the abovementioned meanings
(Chem. Reviews 52, 237–416 (1953)).

Some of the benzylthio-carboxylic halides of the formula (XXXI) are known and/or can be prepared by known processes (J. Antibiotics (1983), 26, 1589).

The halogenocarbonyl ketenes of the formula (V) which are required as starting substances in the above process (E) are new. They can be prepared in a simple manner by methods known in principle (cf., for example, Org. Prep. Proced. Int. 7, (4), 155–158, 1975 and DE 1 945 703). Thus, for example, the compounds of the formula (V)

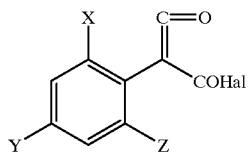

(V)

in which
X, Y and Z have the abovementioned meanings and
Hal represents chlorine or bromine
are obtained when
substituted phenylmalonic acids of the formula (XXXII)

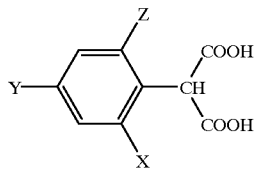

(XXXII)

in which
X, Y and Z have the abovementioned meanings
are reacted with acid halides, such as, for example, thlionyl chloride, phosphorus(V) chloride, phosphorus(III) chloride, oxalyl chloride, phosgene or thionyl bromide, if appropriate in the presence of catalysts, such as, for example, diethylformamide, methyl-sterylformamide or triphenylphosphine, and, if appropriate, in the presence of bases, such as, for example, pyridine or triethylamine.

The substituted phenylmalonic acids of the formula (XXXII) are new and can be prepared in a simple manner by known processes (cf., for example, Organikum [Laboratory Practical in Organic Chemistry], VEB Deutscher Verlag der Wissenschaften, Berlin 1977, p. 517 et seq.).

The carbonyl compounds of the formula (VIII)

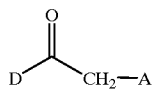

(VIII)

in which
A and D have the abovementioned meanings
or their silyl enol ethers of the formula (VIIIa)

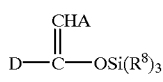

(VIIIa)

in which
A, D and R$^8$ have the abovementioned meanings
and which are required as starting substances for process (E) according to the invention
are compounds which are commercially available, generally known or accessible by known processes.

The preparation of the ketene acid chlorides of the formula (V) which are required as starting substances for carrying out process (F) according to the invention have already been described in process (E) according to the invention. The thioamides of the formula (IX)

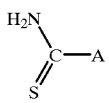
(IX)

in which
A has the abovementioned meaning
and which are required for carrying out process (F) according to the invention
are compounds generally known in organic chemistry.

The compounds of the formula (I-4-a) which are required as starting substances in process (G) are known and/or can be prepared in a simple manner by known methods (cf. WO 92/16510).

The compounds of the formula (I-4-a) are obtained, for example, when compounds of the formula (V)

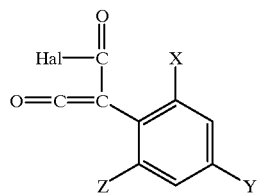
(V)

in which
X, Y and Z have the abovementioned meanings and
Hal represents halogen (in particular chlorine or bromine)
or
compounds of the formula (VI)

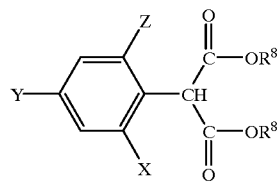
(VI)

in which
$R^8$, X, Y and Z have the abovementioned meanings
are reacted with hydrazines of the formula (VII)

A—NH—NH—D  (VII)

in which
A and D have the abovementioned meanings,
at temperatures between −20° C. and 250° C., preferably between 0° C. and 150° C.,
if appropriate in the presence of a diluent,
it being possible for the following to be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and, only in the event that compounds of the formula (VI) are employed, alcohols, such as methanol, ethanol, propanol, iso-propanol, butanol, iso-butanol and tert-butanol, and, if appropriate, in the presence of a base, where, in the event that compounds of the formula (V) are employed, inorganic bases are suitable, in particular alkali metal carbonates or alkaline earth metal carbonates, such as sodium carbonate, potassium carbonate or calcium carbonate, and organic bases, such as, for example, pyridine or triethylamine, and, in the event that compounds of the formula (VI) are employed, suitable bases being the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine), alkali metals, such as sodium or potassium, the amides and hydrides of alkali metals and alkaline earth metals, such as sodium amide, sodium hydride and calcium hydride, and furthermore also alkali metal alcoholates, such as sodium methoxide, sodium ethoxide and potassium tert-butoxide.

The malonic esters of the formula (VI)

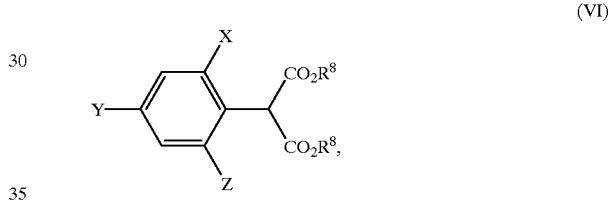
(VI)

in which
$R^8$, X, Y and Z have the abovementioned meanings, are new.

They can be synthesized by generally known methods of organic chemistry (cf., for example, Tetra hedron Lett. 27 2763 (1986) and Org anikum VEB [Laboratory Practical in Organic Chemistry] Deutscher Verlag der Wissenschaften, Berlin 1977, p. 587 et seq.).

Some of the hydrazines of the formula (VII)

A—NH—NH—D  (VII)

in which
A and D have the abovementioned meanings
are known and/or can be prepared by methods known from the literature (cf., for example, Liebigs Ann. Chem. 585 6 (1954); Reaktionen der organischen Synthese [Reactions in Organic Synthesis], C. Ferri, page 212, 513; Georg Thieme Verlag Stuttgart, 1978; Liebigs Ann. Chem. 443, 242 (1925); Chem. Ber. 98, 2551 (1965), EP 508 126).

The acid halides of the formula (X), carboxylic anhydrides of the formula (XI), chloroformic esters or chloroformic thioesters of the formula (XII), chloromonothioformic esters or chlorodithioformic esters of the formula (XIII), alkyl halides of the formula (XIV), sulphonyl chlorides of the formula (XV), phosphorus compounds of the formula (XVI), metal hydroxides, metal alkoxides or amines of the formulae (XVII) and (XVIII), isocyanates of the formula (XIX) and carbamoyl chlorides of the formula (XX), which are furthermore required as starting substances for carrying out processes (G), (H), (I), (J), (K), (L) and (M) according to the invention are generally known compounds of organic or inorganic chemistry.

The compounds of the formulae (VII), (VIII), (IX) to (XXI), (XXIV) and (XXXII) to (XXXIV) have furthermore been disclosed in the patent applications cited at the outset and/or can be prepared by the methods given therein.

Process (A) is characterized in that compounds of the formula (II) in which A, B, D, X, Y, Z and $R^8$ have the abovementioned meanings are subjected to an intramolecular condensation in the presence of a base.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols, such as methanol, ethanol, propanol, isopropanol, butanol, iso-butanol and tert-butanol.

Bases (deprotonating agents) which can be employed when carrying out process (A) according to the invention are all customary proton acceptors. The following can preferably be used: oxides, hydroxides and carbonates of alkali metal and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethyl-benzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals, such as sodium or potassium, can furthermore be used. Other substances which can be employed are amides and hydrides of alkali metals and alkaline earth metals, such as sodium amide, sodium hydride and calcium hydride, and furthermore also alkali metal alcoholates, such as sodium methoxide, sodium ethoxide and potassium tert-butoxide.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formula (II) and the deprotonating bases are generally employed in approximately equimolar to twice the equimolar amounts. However, it is also possible to use one or the other component in a larger excess (up to 3 mol).

Process (B) is characterized in that compounds of the formula (III) in which A, B, X, Y, Z and $R^8$ have the abovementioned meanings are subjected to an intramolecular condensation in the presence of a diluent and in the presence of a base.

Diluents which can be employed in process (B) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone. Other substances which can be employed are alcohols, such as methanol, ethanol, propanol, iso-propanol, butanol, iso-butanol and tert-butanol.

Bases (deprotonating agents) which can be employed when carrying out process (B) according to the invention are all customary proton acceptors. The following can preferably be used: oxides, hydroxides and carbonates of alkali metal and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts, such as, for example, triethyl-benzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals, such as sodium or potassium, can furthermore be used. Other substances which can be employed are amides and hydrides of alkali metals and alkaline earth metals, such as sodium amide, sodium hydride and calcium hydride, and furthermore also alkali metal alcoholates, such as sodium methoxide, sodium ethoxide and potassium tert-butoxide.

When carrying out process (B) according to the invention, the reaction temperatures can be varied within a substantial range. In general, the process is carried out at temperatures between 0° C. and 250° C., preferably between 50° C. and 150° C.

Process (B) according to the invention is generally carried out under atmospheric pressure.

When carrying out process (B) according to the invention, the reactants of the formula (III) and the deprotonating bases are generally employed in approximately equimolar amounts. However, it is also possible to use one or the other component in a larger excess (up to 3 mol).

Process (C) is characterized in that compounds of the formula (IV) in which A, B, W, X, Y, Z and $R^8$ have the abovementioned meanings are subjected to an intramolecular cyclization in the presence of an acid and, if appropriate, in the presence of a diluent.

Diluents which can be employed in process (C) according to the invention are all inert organic solvents. The following can preferably be used: hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methyl-pyrrolidone. Other substances which can be employed are alcohols, such as methanol, ethanol, propanol, iso-propanol, butanol, isobutanol or tert-butanol.

If appropriate, the acid employed may also act as the diluent.

Acids which can be employed in process (C) according to the invention are all customary inorganic and organic acids, such as, for example, hydrohalic acids, sulphuric acids, alkyl-, aryl- and haloalkylsulphonic acids, in particular halogenated alkylcarboxylic acids, such as, for example, trifluoroacetic acid.

When carrying out process (C) according to the invention, the reaction temperatures can be varied within a substantial range. In general, the process is carried out at temperatures between 0° C. and 250° C., preferably between 50° C. and 150° C.

Process (C) according to the invention is generally carried out under atmospheric pressure.

When carrying out process (C) according to the invention, the reactants of the formula (IV) and the acid are employed, for example, in equimolar amounts. If appropriate, however, it is also possible to use the acid as the solvent or the catalyst.

Process (E) according to the invention is characterized in that carbonyl compounds of the formula (VIII) are reacted with ketene acid halides of the formula (V), if appropriate in the presence of a diluent and if appropriate in the presence of an acid acceptor.

Diluents which can be employed in process (E) according to the invention are all inert organic solvents. The following can preferably be used: hydrocarbons, such as toluene and xylene, furthermore ethers, such as dibutyl ether, glycol dimethyl ether and diglycol dimethyl ether, furthermore polar solvents, such as dimethyl sulphoxide, sulpholane, dimethylformamide or N-methyl-pyrrolidone.

Acid acceptors which can be used for carrying out the process variant E) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline.

When carrying out process variant E) according to the invention, the reaction temperatures can be varied within a substantial range. The process is expediently carried out at temperatures between 0° C. and 250° C., preferably between 50° C. and 220° C.

Process (E) according to the invention is expediently carried out under atmospheric pressure.

When carrying out process (E) according to the invention, the reactants of the formulae (VIII) and (V) in which A, D, X, Y and Z have the abovementioned meanings and Hal represents halogen and, if appropriate, the acid acceptors are generally employed in approximately equimolar amounts. However, it is also possible to use one or the other component in a larger excess (up to 5 mol).

Process (F) according to the invention is characterized in that thioamides of the formula (IX) are reacted with ketene acid halides of the formula (V), if appropriate in the presence of a diluent and if appropriate in the presence of an acid acceptor.

Diluents which can be employed in process variant F) according to the invention are all inert organic solvents. The following can preferably be used: hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Acid acceptors which can be used for carrying out process (F) according to the invention are all customary acid acceptors.

The following can preferably be used: tertiary amines, such as triethylamine, pyridine, diazabicyclooctane (DABCO), diazabicycloundecane (DBU), diazabicyclononene (DBN), Hünig base and N,N-dimethyl-aniline.

When carrying out process (F) according to the invention, the reaction temperatures can be varied within a substantial range. The process is expediently carried out at temperatures between 0° C. and 250° C., preferably between 20° C. and 220° C.

Process (F) according to the invention is expediently carried out under atmospheric pressure.

When carrying out process (F) according to the invention, the reactants of the formulae (IX) and (V) in which A, X, Y and Z have the abovementioned meanings and Hal represents halogen, and, if appropriate, the acid acceptors, are generally employed in approximately equimolar amounts. However, it is also possible to use one or the other component in a larger excess (up to 5 mol).

Process (Gα) is characterized in that compounds of the formulae (I-1-a) to (I-6-a) are reacted in each case with carboxylic acid halides of the formula (X), if appropriate in the presence of a diluent and if appropriate in the presence of an acid-binding agent.

Diluents which can be employed in process (Gα) according to the invention are all solvents which are inert to the acid halides. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, nitriles, such as acetonitrile, furthermore ethers, such as diethyl ether, tetrahydrofuran and dioxane, in addition carboxylic esters, such as ethyl acetate, and also strongly polar solvents, such as dimethyl sulphoxide and sulpholane. If the acid halide is sufficiently stable to hydrolysis, the reaction can also be carried out in the presence of water.

Suitable acid-binding agents in the reaction in accordance with process (Gα) according to the invention are all customary acid acceptors. The following can preferably be used: tertiary amines, such as triethylamine, pyridine, diazabicyclooctane (DABCO), diazabicycloundecane (DBU), diazabicyclononene (DBN), Honig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in process (Gα) according to the invention can be varied within a substantial range. In general, the process is carried out at temperatures between −20° C. and +150° C., preferably between 0° C. and 100° C.

When carrying out process (Gα) according to the invention, the starting substances of the formulae (I-1-a) to (I-6-a) and the carbonyl halide of the formula (X) are generally used in approximately equivalent amounts in each case. However, it is also possible to employ the carbonyl halide in a larger excess (up to 5 mol). Working-up is carried out by customary methods.

Process (Gβ) is characterized in that compounds of the formulae (I-1-a) to (I-6-a) are reacted with carboxylic anhydrides of the formula (XI), if appropriate in the presence of a diluent and if appropriate in the presence of an acid-binding agent.

Diluents which can preferably be used in process (Gβ) according to the invention are those which are also preferably suitable when using acid halides. Besides, a carboxylic anhydride employed in excess may also simultaneously act as the diluent.

Optionally added acid-binding agents in process (Gβ) are preferably those acid-binding, agents which are also preferably suitable when using acid halides.

The reaction temperatures in process (Gβ) according to the invention can be varied within a substantial range. In general, the process is carried out at temperatures between −20° C. and +150° C., preferably between 0° C. and 100° C.

When carrying out process (Gβ) according to the invention, the starting substances of the formulae (I-1-a) to (I-6-a) and the carboxylic anhydride of the formula (XI) are generally employed in each case approximately equivalent amounts. However, it is also possible to employ the carboxylic anhydride in a larger excess (up to 5 mol). Working-up is carried out by customary methods.

In general, a procedure is followed in which diluent and carboxylic anhydride, which is present in excess, and the carboxylic acid which forms are removed by distillation or by washing with an organic solvent or with water.

Process (H) is characterized in that compounds of the formulae (I-1-a) to (I-6-a) are reacted in each case with chloroformic esters or chloroformic thiolesters of the formula (XII), if appropriate in the presence of a diluent and if appropriate in the presence of an acid-binding agent.

Suitable acid-binding agents for the reaction in accordance with process (H) according to the invention are all customary acid acceptors. The following can preferably be used: tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Diluents which can be employed in process (H) according to the invention are all solvents which are inert to the chloroformic esters or chloroformic thioesters. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, nitriles, such as acetonitrile, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out process (H) according to the invention, the reaction temperatures can be varied within a substantial range. If the process is carried out in the presence of a diluent and of an acid-binding agent, the reaction temperatures are generally between −20° C. and +100° C., preferably between 0° C. and 50° C.

Process (H) according to the invention is generally carried out under atmospheric pressure.

When carrying out process (H) according to the invention, the starting substances of the formulae (I-1-a) to (I-6-a) and the respective chloroformic ester or chloroformic thiolester of the formula (XII) are generally used in in each case approximately equivalent amounts. However, it is also possible to employ one or the other component in a larger excess (up to 2 mol). Working-up is carried out by customary methods. In general, a procedure is followed in which salts which have precipitated are removed and the reaction mixture which remains is concentrated by stripping off the diluent.

Process (I) according to the invention is characterized in that compounds of the formulae (I-1-a) to (I-6-a) are reacted in each case with (Iα) compounds of the formula (XIII) in the presence of a diluent and, if appropriate, in the presence of an acid-binding agent, or (Iβ) carbon disulphide and subsequently with alkyl halides of the formula (XIV).

In preparation process (Iα), approximately 1 mol of chloromonothioformic ester or chlorodithioformic ester of the formula (XIII) is reacted per mole of starting compounds of the formulae (I-1-a) to (I-6-a) at 0 to 120° C., preferably at 20 to 60° C.

Suitable diluents which are optionally added are all inert polar organic solvents, such as ethers, nitrites, ketones, carboxylic esters, amides, sulphones, sulphoxides, but also halogenoalkanes.

Dimethyl sulphoxide, tetrahydrofuran, ethyl acetate, dimethyl formamide or methylene chloride are preferably employed.

If, in a preferred embodiment, the enolate salt of the compounds (I-1-a) to (I-6-a) is prepared by adding strong deprotonating agents, such as, for example, sodium hydride or potassium tertiary butoxide, the further addition of acid-binding agents can be dispensed with.

If acid-binding agents are employed, then suitable substances are customary inorganic or organic bases, examples of which may be mentioned being sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods.

In preparation process (Iβ), the equimolar amount or an excess of carbon disulphide is added per mole of starting, compounds of the formulae (I-1-a) to (I-6-a). This process is preferably carried out at temperatures from 0 to 50° C., in particular at 20 to 30° C.

Frequently, it is expedient first to prepare the corresponding salt from the compounds of the formulae (I-1-a) to (I-6-a) by adding a base (such as, for example, potassium tertiary-butylate or sodium hydride). The compounds (I-1-a) to (I-6-a) are reacted with carbon disulphide until the formation of the intermediate is complete, for example after stirring at room temperature for several hours.

Bases which can furthermore be employed in process (Iβ) are all customary proton acceptors. The following can preferably be used: alkali metal hydrides, alkali metal alcoholates, alkali metal carbonates, alkali metal hydrogen carbonates, alkaline earth metal carbonates or alkaline earth metal hydrogen carbonates, or nitrogen bases. Examples which may be mentioned are sodium hydride, sodium methanolate, sodium hydroxide, calcium hydroxide, potassium carbonate, sodium hydrogen carbonate, triethylamine, dibenzylamine, dilsopropylamine, pyridine, quinoline, diazabicyclooctane (DABCO), diazabicyclononene (DBN) and diazabicycloundecene (DBU).

Diluents which can be employed in this process are all customary solvents.

The following can preferably be used: aromatic hydrocarbons, such as benzene or toluene, alcohols, such as methanol, ethanol, isopropanol or ethylene glycol, nitriles, such as acetonitrile, ethers, such as tetrahydrofuran or dioxane, amides, such as dimethylformamide, or other polar solvents, such as dimethyl sulphoxide or sulpholane.

The further reaction with the alkyl halide of the formula (XIV) is preferably carried out at 0 to 70° C., in particular 20 to 50° C. At least the equimolar amount of alkyl halide is employed.

The process is carried out under atmospheric pressure or under elevated pressure, preferably under atmospheric pressure.

Again, working-up is carried out by customary methods.

Process (J) according to the invention is characterized in that compounds of the formulae (I-1-a) to (I-6-a) are reacted in each case with sulphonyl chlorides of the formula (XV), if appropriate in the presence of a diluent and if appropriate in the presence of an acid-bindincy agent.

In preparation process (J), approximately 1 mol of sulphonyl chloride of the formula (XV) is reacted per mole of starting compounds of the formulae (I-1-a) to (I-6-a) at −20 to 150° C., preferably at 20 to 70° C.

Suitable diluents which are optionally added are all inert polar organic solvents, such as ethers, amides, ketones, carboxylic esters, nitrites, sulphones, sulphoxides, or halogenated hydrocarbons, such as methylene chloride.

Dimethyl sulphoxide, ethyl acetate, acetonitrile, tetrahydrofuran, dimethylformamide or methylene chloride are preferably employed.

If, in a preferred embodiment, the enolate salt of the compounds (I-1-a) to (I-6-a) is prepared by adding strong deprotonating agents (such as, for example, sodium hydride or potassium tertiary butoxide), the further addition of acid-binding agents can be dispensed with.

If acid-binding agents are employed, then suitable substances are customary inorganic or organic bases, examples which may be mentioned being sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods.

Process (K) according to the invention is characterized in that compounds of the formulae (I-1-a) to (I-6-a) are reacted in each case with phosphorus compounds of the formula (XVI), if appropriate in the presence of a diluent and if appropriate in the presence of an acid-binding agent.

In preparation process (K), 1 to 2, preferably 1 to 1.3, mol of the phosphorus compound of the formula (XVI) are reacted per mole of the compounds of the formulae (I-1-a) to (I-6-a) at temperatures between −40° C. and 150° C., preferably between −10 and 110° C., to obtain compounds of the formula (I-1-e) to (I-6-e).

Suitable diluents which are optionally added are all inert, polar organic solvents, such as ethers, amides, ketones, carboxylic esters, nitriles, alcohols, sulphides, sulphones, sulphoxides and the like.

Acetonitrile, dimethyl sulphoxide, ethyl acetate, tetrahydrofuran. dimethylformamide or methylene chloride are preferably employed.

Suitable acid-binding agents which are optionally added are customary inorganic or orgyanic bases, such as hydroxides, carbonates or amines. Examples which may be mentioned are sodium hydroxide, sodium carbonate, potassium carbonate, pyridine and triethylamine.

The reaction can be carried out under atmospheric pressure or under elevated pressure, it is preferably carried out under atmospheric pressure. Working-up is carried out by customary methods of organic chemistry. The end products obtained are preferably purified by crystallization, chromatography or by so-called "incipient distillation", i.e. removal of the volatile components in vacuo.

Process (L) is characterized in that compounds of the formulae (I-1-a) to (I-6-a) are reacted with metal hydroxides or metal alkoxides of the formula (XVII) or amines of the formula (XVIII), if appropriate in the presence of a diluent.

Diluents which can be employed in process (L) according to the invention are, preferably, ethers, such as tetrahydrofuran, dioxane, diethyl ether, or else alcohols, such as methanol, ethanol, isopropanol, but also water. Process (L) according to the invention is generally carried out under atmospheric pressure. The reaction temperatures are generally between −20° C. and 100° C., preferably between 0° C. and 50° C.

Process (M) according to the invention is characterized in that compounds of the formulae (I-1-a) to (I-6-a) are reacted in each case with (Mα) compounds of the formula (XIX), if appropriate in the presence of a diluent and if appropriate in the presence of a catalyst, or (Mβ) with compounds of the formula (XX), if appropriate in the presence of a diluent and if appropriate in the presence of an acid-binding, agent.

In preparation process (Mα), approximately 1 mol of isocyanate of the formula (XIX) is reacted per mole of starting compounds of the formulae (I-1-a) to (I-6-a) at 0 to 100° C., preferably at 20 to 50° C.

Suitable diluents which are optionally added are all inert organic solvents, such as ethers, amides, nitrites, ketones, carboxylic esters, sulphones or sulphoxides.

If appropriate, catalysts may be added to accelerate the reaction. Catalysts which can be employed very advantageously are organotin compounds, such as, for example, dibutyltin dilaurate. The process is preferably carried out under atmospheric pressure.

In preparation process (Mβ), approximately 1 mol of carbamoyl chloride of the formula (XX) is reacted per mole of starting compounds of the formulae (I-1-a) to (I-6-a) at 0 to 150° C., preferably at 20 to 70° C.

The diluents which are optionally added are all inert polar organic solvents, such as ethers, amides, ketones, carboxylic esters, sulphones, sulphoxides or halogenated hydrocarbons.

Dimethyl sulphoxide, tetrahydrofuran, ethyl acetate, dimethylformamide or methylene chloride are preferably employed.

If, in a preferred embodiment, the enolate salt of the compounds (I-1-a) to (I-6-a) is prepared by adding strong deprotonating agents (such as, for example, sodium hydride or potassium tertiary-butoxide), a further addition of acid-binding agents can be dispensed with.

If acid-binding agents are employed, then suitable substances are customary inorganic or organic bases, examples which may be mentioned being sodium hydroxide, sodium carbonate, potassium carbonate, triethylamine or pyridine.

The reaction can be carried out under atmospheric pressure or under elevated pressure, it is preferably carried out under atmospheric pressure. Working-up is carried out by customary methods.

The active compounds are suitable for combating animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hya-*

*lopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa gpp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, Oscinella frit, Phorbia spp., *Pegomyla hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention are distinguished by a high insecticidal and acaricidal activity.

They can be employed particularly successfully for combating plant-damaging insects, such as, for example, against the larvae of the mustard beetle (*Phaedon cochleariae*) or ag,ainst the larvae of the green rice leafhopper (*Nephotettix cincticeps*) or against the caterpillars of the diamond-back moth (*Plutella maculipennis*).

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according, to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

The active compounds according to the invention are highly suitable for selectively combating monocotyledon weeds in dicotyledon cultures by the pre-and postemergence methods. For example, they can be employed very successfully in cotton or sug,ar beet for combating grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as ,um arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compounds can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous components are the following:
Fungicides:
2-aminobutane, 2-anilino-4-methyl-6-cyclopropyl-pyrimidine; 2',6'-dibromo-2-methyl-4'-trifluoromethoxy-4'-trifluoro-methy-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithi ocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichliamide, tricyclazole, tridemorph, triflumizole, triforine, triticonazole, validamycin A, vinclozolin, zineb, ziram.
Bactericides:
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.
Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulphotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

For example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and loxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuron-methyl; thiocarbamates such as, for example, butylate, cycloate, diallate, EPTC, esprocarb, molinate, prosulphocarb, thiobencarb and triallate; triazines such as, for example, atrazine, cyanazine, simazine, simetryne, terbutryne and terbuthylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according, to the invention are not only active against plant, hygiene and stored-product pests, but also, in the veterinary medicine sector, against animal parasites (ectoparasites), such as ixodid ticks, argasid ticks, scab mites, trombi culid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hi ppobosca pp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp and Panstrongylus spp.

From the order of the Blattarida, for example, Blatta orientalis, Periplaneta americana, Blattela germanica and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show an outstanding activity against *Boophilus microplus.*

The active compounds of the formula (I) according to the invention are also suitable for combating arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80%, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec., *Dinoderus minutus*.

Dermapterans, such as *Sirex juvencus, Urocerus gigas, Urocerus gigas taignus, Urocerus augur*.

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*.

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the artificial resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indenelcoumarone resin, silicone resin, drying vegetable and/or drying oils and/or physically drying binders based on a natural and/or artificial resin.

The artificial resin used as the binder can be employed in the form of an emulsion, dispersion or solution. Up to 10% of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a dryingy vegetable oil as the organochemical binder. Preferably used according to the invention are alkyd resins with an oil content of over 45% by weiht, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight -glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalit, dichlofluanid, tolylfluanid, 3-iodo-2-propinylbutyl carbam ate, N-octyl-isothiazolin-3-one and 4,5-dichloro-N-octylisothiazolin-3-one The preparation and the use of the active compounds according, to the invention can be seen from the examples which follow.

PREPARATION EXAMPLES

Example (I-1-a-1)

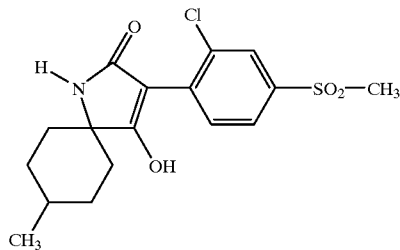

(I-1-a-1)

3.2 g (0.028 mol) of potassium tert-butoxide are introduced into 10 ml of absolute tetrahydrofuran (THF). 5.1 g (0.0127 mol) of the compound of Example (II-1) in 30 ml of absolute toluene are added dropwise at reflux temperature, and the mixture is stirred for another 1.5 hours under reflux. Then, 20 ml of water are added, the phases are separated, the toluene phase is extracted using 10 ml of water, and the combined water phases are washed using toluene. The aqueous phase is acidified with approximately 2.3 ml of concentrated hydrochloric acid at 15° C. to 20° C. The precipitate is filtered off with suction, washed, dried and recrystallized from methyl tert-butyl ether (MTB ether)/n-hexane. Yield: 4.4 g (93% of theory), m.p. 222° C.

The compounds of the formula (I-1-a) given in the table which follows were prepared analogously to or in accordance with the general preparation instructions:

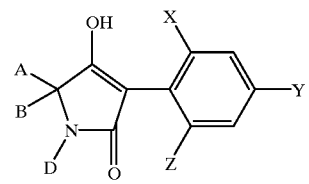

(I-1-a)

| Ex. No. | X | Y | Z | A | B | D | M.p. ° C. | Isomer |
|---|---|---|---|---|---|---|---|---|
| I-1-a-2 | CH$_3$ | CN | CH$_3$ | CH$_3$ | CH$_3$ | H | >220 | — |
| I-1-a-3 | CN | CH$_3$ | CH$_3$ | CH$_3$ | CH$_3$ | H | >220 | — |
| I-1-a-4 | CN | CH$_3$ | CH$_3$ | —(CH$_2$)$_2$—CHCH$_3$—(CH$_2$)$_2$— | | H | >220 | β |
| I-1-a-5 | C$_2$H$_5$ | CN | CH$_3$ | —(CH$_2$)$_2$—CHCH$_3$—(CH$_2$)$_2$— | | H | >220 | β |
| I-1-a-6 | CH$_3$ | CN | CH$_3$ | —(CH$_2$)$_2$—CHCH$_3$—(CH$_2$)$_2$— | | H | >220 | β |
| I-1-a-7 | C$_2$H$_5$ | CN | C$_2$H$_5$ | —(CH$_2$)$_2$—CHCH$_3$—(CH$_2$)$_2$— | | H | >220 | β |
| I-1-a-8 | OCH$_2$CF$_3$ | CH$_3$ | CH$_3$ | —(CH$_2$)$_2$—CHCH$_3$—(CH$_2$)$_2$— | | H | >220 | β |

Example (I-1-b-1)

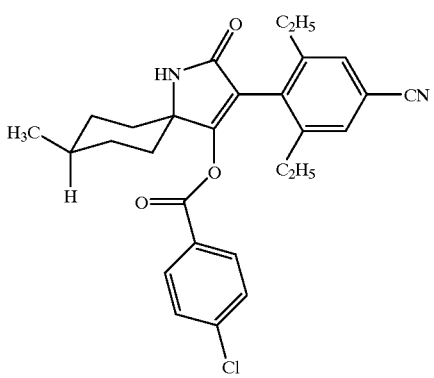

2.03 g of the compound of Example (I-1-a-7) and 8.5 ml of triethylamine in 50 ml of methylene chloride are treated with 0.8 ml of 4-chlorobenzoyl chloride in 5 ml of methylene chloride at 0° C. to 10° C., and the mixture was stirred at room temperature until the reaction had ended (TLC check). The mixture is washed twice using 30 ml of 0.5N NaOH, dried and concentrated. The residue is recrystallized from MTB ether/n-hexane.

This gives 1.6 g (55% of theory) of m.p.: >220° C.

The following compounds of the formula (I-1-b) are obtained analogously to or in accordance with the general preparation instructions:

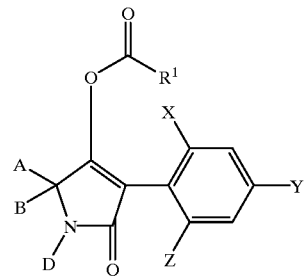

(I-1-b)

| Ex. No. | X | Y | Z | A | B | D | $R^1$ | M.p. [° C.] | Isomer |
|---|---|---|---|---|---|---|---|---|---|
| I-1-b-2 | $C_2H_5$ | CN | $C_2H_5$ | —(CH$_2$)$_2$—CHCH$_3$—(CH$_2$)$_2$— | | H | i-C$_3$H$_7$ | >220 | β |
| I-1-b-3 | $C_2H_5$ | CN | $C_2H_5$ | —(CH$_2$)$_2$—CHCH$_3$—(CH$_2$)$_2$— | | H | $C_2H_5$—O—CH$_2$— | 214 | β |
| I-1-b-4 | $C_2H_5$ | CN | $C_2H_5$ | —(CH$_2$)$_2$—CHCH$_3$—(CH$_2$)$_2$— | | H | 2-Cl-5-pyridyl | >220 | β |

Example (I-1-c-1)

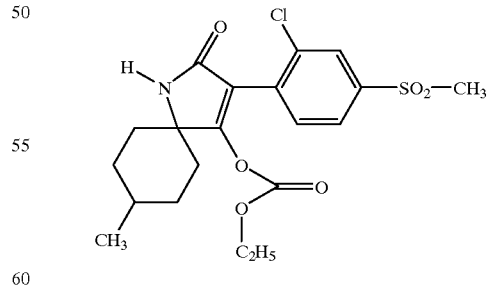

(I-1-c-1)

3.33 g (0.009 mot) of the compound of Example (I-1-a-1) In 50 ml of absolute methylene chloride are first treated with 1.3 ml of triethylamine and then, at 0° C. to 10° C., with 0.9 ml of ethyl chloroformate in 5 ml of absolute methylene chloride. The mixture is stirred at room temperature until the reaction has ended (TLC check). It is then washed twice using 50 ml of 0.5N NaOH, dried and evaporated. The residue is recrystallized from MTB ether/n-hexane. Yield: 2.50 (g (62% of theory), m.p. 211° C.

The following compounds of the formula (I-1-c) were obtained analogously to or in accordance with the general preparation instructions:

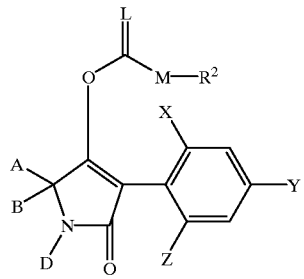

(I-1-c)

| Ex. No. | X | Y | Z | A | B | D | L | M | R² | M.p. [° C.] | Isomer |
|---|---|---|---|---|---|---|---|---|---|---|---|
| I-1-c-2 | C₂H₅ | CN | C₂H₅ | —(CH₂)₂—CHCH₃—(CH₂)₂— | | H | O | O | Benzyl | 209 | β |
| I-1-c-3 | C₂H₅ | CN | C₂H₅ | —(CH₂)₂—CHCH₃—(CH₂)₂— | | H | O | O | Benzyl | >220 | β |

Example I-2-a-1

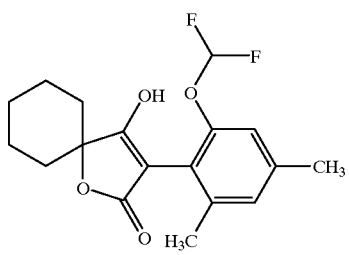

7.7 g (0.02 mol) of the compound of Example (III-1), dissolved in a small amount of THF, are added dropwise to 3.4 g (0.03 mol) of potassium tert-butoxide in 50 ml of THF. The mixture is subsequently stirred overnight at room temperature. It is then poured into water, acidified and extracted using methylene chloride, and the organic phase is dried and concentrated. The crude product is triturated with ether and filtered off with suction. To purify the product further, it is chromatographed on silica gel using cyclohexane/ethyl acetate 1/1 as the eluent.

Example I-2-a-2

The following compound is obtained analogously to Example I-2-a-1.

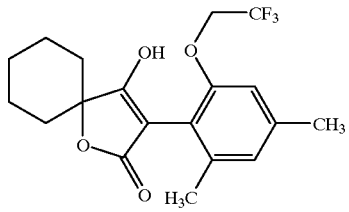

M.p. 185 to 187° C.

Example I-2-b-1

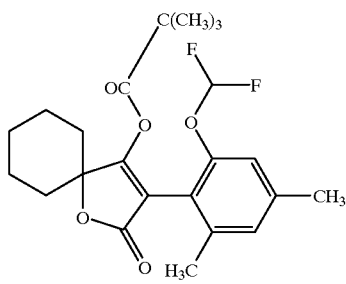

1.2 g (3.5 mmol) of the compound of Example I-2-a-1, 0.4 g (3.9 mmol) of triethylamine and a small amount of DABCO are introduced into 20 ml of THF. 0.43 g (3.5 mmol) of pivaloyl chloride is added dropwise at 0° C. to 10° C., and the mixture is stirred overnight under reflux. The mixture is concentrated and partitioned between water and methylene chloride, and the organic phase is dried and concentrated. Yield: 1.23 g (83% of theory), m.p. 144° C.

Example I-2-b-2

The compound

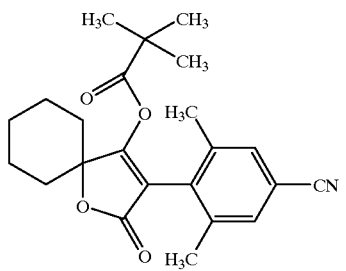

is obtained analogously to Example I-2-b-1.
M.p. 143 to 147° C.

Example I-2-b-3

The compound

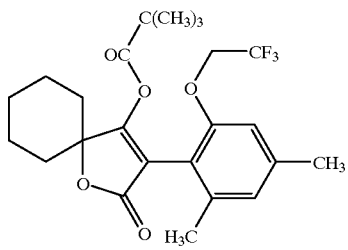

is obtained analogously to Example I-2-b-1.

Example (I-1) (β)

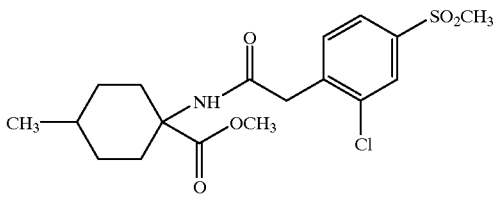

6.77 g (0.0396 mol) of methyl 4-methylcyclohexylamine-1-carboxylate In 65 ml of absolute THF are treated with 9.13 ml (0.065 mol) of triethylamine. After 5 minutes, 8.1 g

Example (II-2)

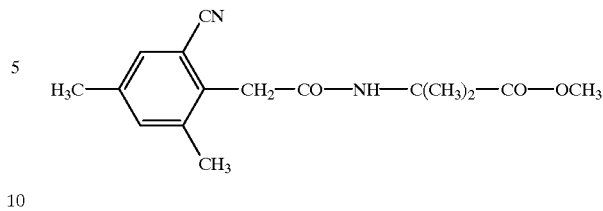

7 g of 2-cyano-4,6-dimethylphenylacetic acid and 8.2 ml of thionyl chloride are stirred at 80° C. until the evolution of gas has ceased. The excess thionyl chloride is distilled off and the residue is taken up in 30 ml of dry THF. This solution is added dropwise at 0° C. to 10° C. to a mixture of 8.52 g of the compound of the formula

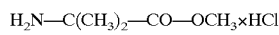

and 17 ml of triethylamine in 120 ml of anhydrous THF, and the mixture is stirred for one hour at room temperature. It is subsequently evaporated, the residue is taken up in methylene chloride, and the mixture is washed using 0.5N HCl, dried and reevaporated. The residue is recrystallized from MTB ether/n-hexane.

Yield: 7.6 g (71% of theory), m.p. 141° C.

The compounds of the formula (II) given in the table below were synthesized analogously to or in accordance with the general preparation instructions.

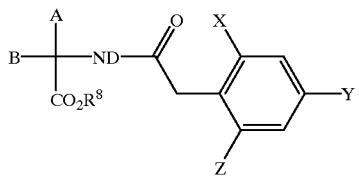

(II)

| Ex. No. | X | Y | Z | A | B | D | R$^8$ | M.p. ° C. | Isomer |
|---|---|---|---|---|---|---|---|---|---|
| II-3 | CH$_3$ | CN | CH$_3$ | CH$_3$ | CH$_3$ | H | CH$_3$ | 132 | |
| II-4 | CN | CH$_3$ | CH$_3$ | —(CH$_2$)$_2$—CHCH$_3$—(CH$_2$)$_2$— | | H | CH$_3$ | 164 | β |
| II-5 | CH$_3$ | CN | CH$_3$ | —(CH$_2$)$_2$—CHCH$_3$—(CH$_2$)$_2$— | | H | CH$_3$ | 195 | β |
| II-6 | C$_2$H$_5$ | CN | CH$_3$ | —(CH$_2$)$_2$—CHCH$_3$—(CH$_2$)$_2$— | | H | CH$_3$ | 161 | β |
| II-7 | OCHF$_2$ | CH$_3$ | CH$_3$ | —(CH$_2$)$_2$—CHCH$_3$—(CH$_2$)$_2$— | | H | CH$_3$ | 121 | β |
| II-8 | OCH$_2$CF$_3$ | CH$_3$ | CH$_3$ | —(CH$_2$)$_2$—CHCH$_3$—(CH$_2$)$_2$— | | H | CH$_3$ | 142 | β |
| II-9 | C$_2$H$_5$ | CN | C$_2$H$_5$ | —(CH$_2$)$_2$—CHCH$_3$—(CH$_2$)$_2$— | | H | CH$_3$ | 167 | β |

(0.0325 mol) of 2-chloro-4-methylsulphonyl-phenylacetic acid of Example (XXVIII-1) are added after 5 minutes, the mixture is stirred at room temperature for 15 minutes, 12.74 ml (0.091 mol) of triethylamine are added, and 3.06 ml of phosphorus oxychloride are immediately added dropwise in such a way that the solution is at a moderate boil. The mixture is stirred for 30 minutes under reflux, poured into 300 ml of ice-water and extracted using methylene chloride, and the methylene chloride phase is dried and evaporated. The residue is purified by column chromatography on silica gel (eluent methylene chloride/ethyl acetate 5/1).

Yield: 5.1 g (39% of theory), oil.

$^1$H NMR (200 MHz, CDCl$_3$): δ=0.89 (d, 3H), 3.05 (s, 3H), 3.67 (s, 3H), 3.75 (s, 2H), 5.95 (br, 1H), 7.6 (d, 1H), 7.8 (dd, 1H), 7.97 (d, 1H).

Example (III-1)

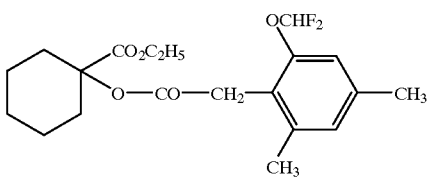

5.33 g (0.031 mol) of ethyl 1-hydroxycyclohexanecarboxylate and 7.7 g (0.031 mol) of the carbonyl chloride of the formula

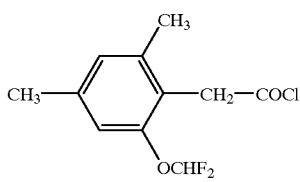

(obtained in the customary manner from the compound of (Example XXVIII-c-1)) are refluxed overnight in 50 ml of toluene, and the mixture is subsequently concentrated. Yield: 11.9 g (quantitative) of an oil.

Example (III-2)

The compound

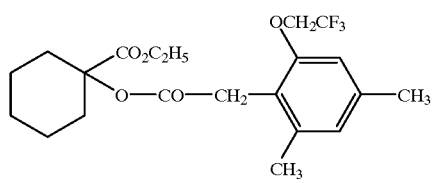

is obtained analogously to Example (III-1) as an oil (yield 93% of theory).

Example (XXVIII-I)

(XXVIII-1)

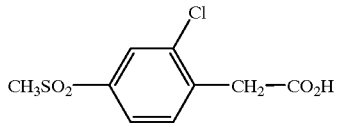

21.3 g (0.1 mol) of 2-chloro-4-methylsulphonyltoluene (known from, for example, DE 39 37 282) are dissolved in 43 ml of carbon tetrachloride, and 18.3 g (0.1 mol) of N-bromosuccinimide are added at room temperature. Thereupon, 0.1 g of AIBN (azo-isobutyronitrile) are also metered in, and the batch is stirred for 7 hours under reflux. It is subsequently subjected to filtration with suction, and the mother liquor is concentrated. This gives 31.3 g of 2-chloro-4-methylsulphonylbenzyl bromide of a purity of 78.6% (87% -of theory).

31.3 g (87 mmol) of 2-chloro-4-methylsulphonyl-benzyl bromide and 1.6 g of tetrabutylammonium sulphate are dissolved in 92 ml of methylene chloride, and a solution of 17 g of potassium cyanide in 70 ml of water is added dropwise at room temperature. Stirring is continued overnight at room temperature, the phases are subsequently separated, and the organic phase is concentrated. After purification over silica gel (eluent methylene chloride), 10.5 g of 2-chloro-4-methylsulphonyl-benzyl cyanide of a purity of 69% are obtained (37% of theory).

10 g (30 mmol) of 2-chloro-4-methylsulphonyl-benzyl cyanide are introduced at 80–90° into a solution of 28.1 ml of concentrated sulphuric acid and 33.8 ml of water, and the mixture is stirred for 2 hours under reflux. The batch is allowed to cool to room temperature and poured into 75 ml of ice-water. The insoluble fraction is filtered off with suction, washed with ice-water and dried. This gives 3.3 g of 2-chloro-4-methylsulphonyl-phenylacetic acid of a purity of 91% (40.2% of theory). Example (XXVIII-c-1)

(XXVIII-c-1)

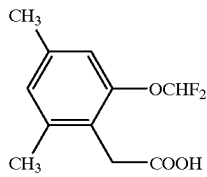

This compound was synthesized via the following route:

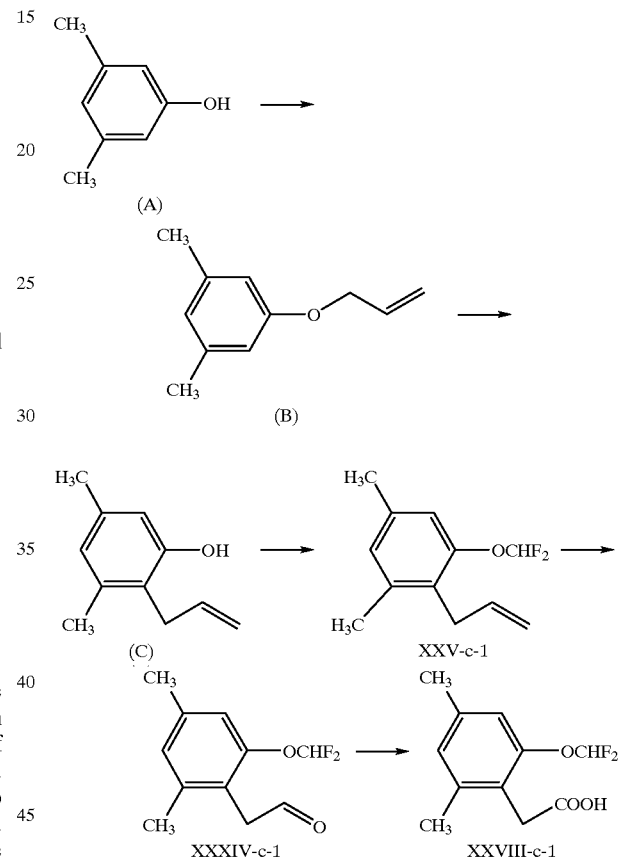

Allyl 3,5-dimethylphenyl ether (B)

(B)

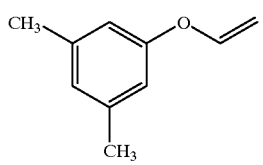

1000 g of 3,5-dimethylphenol (A) were dissolved in 1000 ml of acetone, 980 g of allyl bromide were added dropwise, and 114.8 g of potassium carbonate were subsequently added. The mixture was refluxed for 18 hours and then cooled. The potassium carbonate was filtered off, and the filtrate was treated with 3000 ml of water. It was extracted three times using tert-butyl methyl ether, and the organic phases were combined and washed twice using in each case 300 ml of 10% strength sodium hydroxide solution. The organic phase was dried over potassium carbonate and filtered, and the filtrate was concentrated. After distillation, 837 g (64% of theory) of allyl 3,5-dimethylphenyl ether of a boiling point of 98 to 110° C. at 10 mbar were obtained.

$^1$H NMR (CDCl$_3$): δ=6.61 (s, 1H), 6.57 (s, 2H), 6.06 (ddt. 1H), 5.51–5.20 (m, 2H), 4.51 (dm, 2H), 2.30 ppm (s, 3H).

3,5-Dimethyl-2-(2-propen-1-yl)-phenol (C)

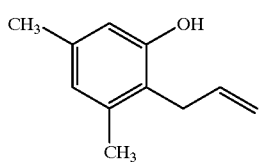

(C)

837 g of allyl 3,5-dimethylphenyl ether (B) were dissolved in 1500 ml of mesitylene, and the solution was refluxed for two days. The solvent was removed in vacuo and the residue was taken up in tert-butyl methyl ether. The mixture was extracted repeatedly using sodium hydroxide solution, and the aqueous phases were combined and acidified with hydrochloric acid. The product which separates out was taken up in tert-butyl methyl ether, and the mixture was dried over magnesium sulphate, concentrated and distilled. A total of 619 g (74% of theory) of 3,5-dimethyl-2-(2-propen-1-yl)-phenol of a boiling point of 145° C. at 30 mbar and a melting point of 51° C. were obtained.

$^1$H NMR (CDCl$_3$): δ=6.61 (s, 1H), 6.51 (s, 1H), 6.10–5.84 (m, 1H), 5.14–4.95 (m, 2H), 3.39 (d, 2H), 2.25 ppm (s, 7H).

3,5-Dimethyl-2-(2-propen-1-yl)-phenyl Difluoromethyl Ether (XXXV-c-1)

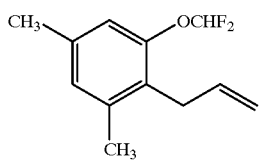

(XXXV-c-1)

125 g of 45% strength sodium hydroxide solution and 10 g of tetrabutyl-ammonium bromide were metered into 100 g of 3,5-dimethyl-2-(2-propen-1-yl)-phenol (C) in 700 ml of toluene. The mixture was heated to 90° C., and 110 g of chlorodifluoromethane were subsequently passed in. After the mixture had cooled to room temperature, 300 ml of water were added, and the toluene phase was separated off. The aqueous phase was extracted twice using 200 ml of tert-butyl methyl ether, and the combined organic phases were dried over sodium sulphate. The mixture was concentrated, and, after distillation, 58.5 g (45% of theory) of 3,5-dimethyl-2-(2-propen-1-yl)-phenyl difluoromethyl ether of a boiling point of 55–65° C. at 0.15 mbar were obtained.

$^1$H NMR (CDCl$_3$): δ=6.83 (s, 1H), 6.75 (s, 1H), 6.37 (t, 1H), 5.91–5.80 (m, 1H), 4.96 (dm, 1H), 4.86 (dm, 1H), 3.48 (d, 2H), 2.26 (s, 3H), 2.24 ppm (s, 3H).

2-Difluoromethyloxy-4,6-dimethylphenylacetaldehyde (XXXIV-c-1)

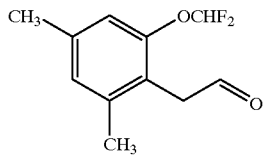

(XXXIV-c-1)

16.5 g of 3,5-dimethyl-2-(2-propen-1-yl)-phenyl difluoromethyl ether were dissolved in 50 ml of dichloromethane and the solution was cooled to −70° C. Ozone was passed through the solution for one hour until the olefin was no longer detectable. The vessel was subsequently flushed with a stream of nitrogen, 13.7 g of dimethyl sulphide were added, and stirring of the mixture was continued for 30 minutes. The solution was warmed to room temperature and stirring was continued for a further 30 minutes. After the solution was free from peroxides, it was concentrated, and the residue was employed in the next reaction without further purification. 19.2 g of 2-difluoromethyloxy-4,6-dimethylphenylacetaidehyde were obtained as crude product.

$^1$H NMR (CDCl$_3$): δ=9.67 (t, 1H), 6.90 (s, IH), 6.81 (s, 1H), 6.47 (t, 1H), 3.78 (d, 2H), 2.32 (s, 3H), 2.28 ppm (s, 3H)

2-Difluoromethyloxy-4,6-dimethylphenylacetic Acid (XXVIII-c-1)

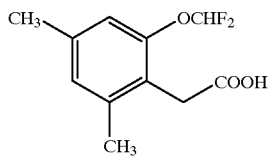

(XXVIII-c-1)

19.2 g of 2-difluoromethyloxy-4,6-dimethylphenylacetaldehyde (XXXIV-c-1) as the crude product were dissolved in 270 ml of tert-butanol, the solution was mixed with 90.4 g of 2-methyl-2-butene, and a solution of 90 g of sodium dihydrogen phosphate and 42 g of sodium chlorite in 353 ml of water was subsequently added dropwise at room temperature. The mixture was stirred for four hours and then stirred into 400 ml of ethyl acetate, and the phases were separated. The aqueous phase was extracted two more times using ethyl acetate, and the combined organic phases were dried over magnesium sulphate and concentrated. After stirring with hexane, 11 g of solid were isolated, from which 2.5 g (14% of theory via 2 steps) of 2-difluoromethyloxy-4,6-dimethylphenylacetic acid of melting point 124–127° C. were obtained.

$^1$H NMR (CDCl$_3$) δ=9.50–8.00 (m, 1H), 6.89 (s, 1H), 6.81 (s, 1H), 6.44 (t, 1H), 3.74 (s, 2H), 2.30 (s, 3H), 2.28 ppm (s, 3H).

Example (XXXV-c-2)

3,5-Dimethyl-2-(2-propen-1-yl)phenyl 2,2,2-trifluoroethyl ether (XXXV-c-2)

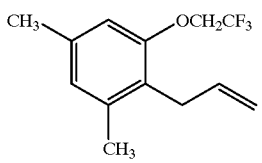
(XXXV-c-2)

17 g of sodium hydroxide were metered into a mixture of 50 g of 3,5-dimethyl-2-(2-propen-1-yl)-phenol (C) and 86 g of 2,2,2-trifluoroethyl tosylate in 450 ml of N-methylpyrrolidone at 120° C. Stirring was continued for 16 hours at 120° C., and the mixture was subsequently poured into 2 l of water. The pH was brought to 2 using 6N hydrochloric acid, and the mixture was extracted using dichloromethane. The combined organic phases were dried over sodium sulphate, the solvent was removed in vacuo, and the residue was distilled. This gave 32 g (43% of theory) of 3,5-dimethyl-2-(2-propen-1-yl)phenyl 2,2,2-trifluoroethyl ether of a boiling point of 100° C. at 1 mbar.

Example (XXIV-c-2)

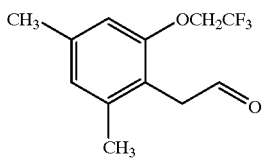
(XXIV-c-2)

obtained analogously to Example (XXIV-c-1).
Crude yield: 28.5 g.

Example (XXVIII-c-2)

Obtained analogously to Example (XXVIII-c-1).

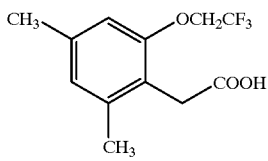
(XXVIII-c-2)

Yield: 12.2 g (52% of theory via 2 steps); M.p. 123–126° C.
$^1$H NMR (CDCl$_3$): δ=6.73 (s, 1H), 6.53 (s, 1H), 4.32 (q, 2H), 3.72 (s, 2H), 2.30 (s, 3H), 2.26 ppm (s, 3H).

Example (XXX-b-1)

Methyl 4-cyano-2-ethyl-6-methyl phenylacetate

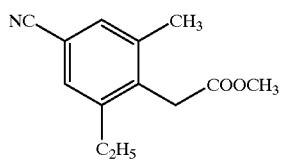
(XXX-b-1)

7.5 of methyl 4-bromo-2-ethyl-6-methylphenylacetate were dissolved in 140 ml of dimethylformamide, 5.5 g of copper cyanide were added, and the mixture was heated for 18 hours at 130° C., until the reaction was complete. The mixture was then cooled to room temperature and diluted with water, and the product was extracted repeatedly using tert-butyl methyl ether. The combined organic phases were dried over magnesium sulphate, concentrated and distilled. This gave 3.4 g (52% of theory) of methyl 4-cyano-2-ethyl-6-methylphenylacetate of a boiling point of 123–130° C. and a melting point of 65–72° C.

$^1$H NMR (CDCl$_3$): δ=7.36 (s, 1H), 7.33 (s, 1H), 3.75 (s, 2H), 3.70 (s, 3H, 2.68 (q, 2H), 2.34 (s, 3H), 1.22 ppm (t, 3H).

The following were obtained analogously:

Example (XXX-b-2)

Methyl 4-cyano-2,6-dimethylphenylacetate

Yield: 17.5 L (45% of theory); B.p. 122–123° C. at 0.09 mbar, m.p.=50–53° C. $^1$H NMR (CDCl$_3$): δ=7.32 (s, 2H), 3.73 (s, 2H), 3.70 (s, 3H), 2.34 ppm (s, 6H)

Example (XXX-b-3)

Methyl 4-cyano-2,6-diethylphenylacetate

B.p. 123–133° C./0.02 mbar; m.p.: 78–81° C. and

Example (XXX-a-1)

Methyl 2-cyano-4,6-dimethylphenylacetate

Yield: 25.3 g (66% of theory) B.p. 78–81° C. $^1$H NMR (CDCl$_3$): δ=7.32 (s, 1H), 7.23 (s, 1H), 3.88 (s, 2H), 3.72 (s, 3H), 2.33) (s, 3H), 2.29 ppm (s, 3H).

Example (XXVIII-a-1)

2-Cyano-4,6-dimethylphenylacetic Acid

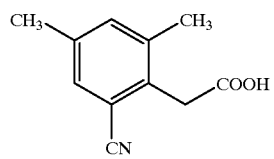
(XXVIII-a-1)

3 g of methyl 2-cyano-4,6-dimethylphenylacetate (XXX-a-I) were dissolved in 50 ml of tetrahydrofuran, treated with a solution of 355 mg of lithium hydroxide in 50 ml of water and stirred for 18 hours at room temperature.

The solvent was subsequently removed in vacuo, the residue was taken up in water, and the neutral substances were removed by extraction using, tert-butyl methyl ether. The aqueous phase was cooled to 0° C. and acidified using 3-molar hydrochloric acid. The product which had precipitated was filtered off with suction, washed with water and dried. 2.5 g (86% of theory) of 2-cyano-4,6-dimethylphenylacetic acid of a melting point of 155–157° C. were isolated.

$^1$H NMR (CDCl$_3$): δ=7.32 (s, 1H), 7.23 (s, 1H), 3.92 (s, 2H), 2.33 (s, 3H), 2.31 ppm (s, 3H).

The following were obtained analogously:

Example (XXVIII-b-1)

4-Cyano-2-ethyl-6-methylphenylacetic Acid

Yield: 1.8 g (64% of theory) M.p.=157–161° C. IR: 2222 cm$^{-1}$ (CN)

$^1$H NMR (CDCl$_3$): δ=7.38 (s, 1H), 7.34 (s, 1H), 3.77 (s, 2H), 2.68 (q, 2H), 2.35 (s, 3H), 1.22 ppm (t, 3H)

Example (XXVIII-b-2)

4-Cyano-2,6-dimethylphenylacetic Acid (XXVIII-b-2)

Yield: 11.8 g (91% of theory) M.p.=202–206° C.

$^1$H NMR (CDCl$_3$): δ=7.34 (s, 2H), 3.77 (s, 2H), 2.36 ppm (s, 6H) and

Example (XXVIII-b-3)

4-Cyano-2,6-diethylphenylacetic Acid

M.p.: 158–162° C.

Use Examples

Example A

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a destruction of at least 85% was caused, after 7 days, for example by the compounds of Preparation Examples I-1-a-1 and I-1-c-1 at an exemplary active compound concentration of 0.1%.

Example B

Nephotettix Test

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice leafhopper (*Nephotettix cinticeps*) while the leaves are still moist.

After the specified period of time, the destruction in % is determined. 100% means that all the leafhoppers have been killed; 0% means that none of the leafhoppers have been killed.

In this test, a destruction of 100% was caused, after 6 days, for example by the compound of Preparation Examples I-1-a-1, I-1-a-4, I-1-a-5 and I-1-a-6 at an exemplary active compound concentration of 0.1%.

Example C

Pre-emergence Test

Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a damage of 80% to Alopecurus myosuroides combined with good tolerance by Beta vulgaris was caused, for example, by the compounds of Preparation Examples I-1-a-1 and I-1-c-1 at an exemplary application rate of 4000 g/ha.

A damage of 80% to Abutilon combined with good tolerance by maize was caused by the compound of Preparation Example I-1-a-6 at an exemplary application rate of 250 g/ha.

A damage of in each case 100% to Alopecurus, Digitaria, Echinochloa, Chenopodium and Veronica combined with good tolerance by soya beans was caused by the compound of Preparation Example I-1-a-4 at an exemplary application rate of 250 g/ha.

Example D

Myzus Test

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Cabbage leaves (*Brassica oleracea*) which are severely infested with peach aphids (*Myzus persicae*) are treated by being dipped into the active compound preparation of the desired concentration.

After the specified period of time, the destruction in % is determined. 100% means that all the aphids have been killed; 0% means that none of the aphids have been killed.

In this test, a destruction of at least 95% was caused, after 6 days, for example by the compounds of Preparation Examples I-1-a-4, I-1-a-5 and I-1-a-6 at an exemplary active compound concentration of 0.01%.

Example E

Tetranychus Test (OP-resistant)

Solvent: 7 parts by weight of dimethylformamide
Emulsifier: 1 part by weight of alkylaryl polyglycol ether To produce a suitable preparation of active compond, 1 part by weight of active compound is mixed with the stated amount of solvent and the stated amount of emulsifier, and the concentrate is diluted with water to the desired concentration.

Bean shoots (*Phaseolus vulgaris*) which are severely infested with the greenhouse red spider mite (*Tetranychus*

95

*urticae*) are dipped into a preparation of the active compound of the desired concentration.

After the specified period of time, the destruction in % is determined. 100% means that all the spider mites have been killed; 0% means that none of the spider mites have been killed.

In this test, an activity of 100% was shown, after 13 days, for example by the compounds of Preparation Examples I-1-a-4, I-1-a-5 and I-1-a-6 at an exemplary active compound concentration of 0.1%.

Example F

Test with *Boophilis microplus* Resistant/SP-resistant Parkhurst Strain

Test animals: adult females which have sucked themselves full

Solvent: dimethyl sulphoxide 20 mg, of active substance are dissolved in 1 ml of dimethyl sulphoxide, and lesser concentrations are prepared by dilution with the same solvent.

The test is carried out in 5 replications. 1 μl of the solutions is injected into the abdomen, and the animals are transferred into dishes and kept in a controlled-environment cabinet. The activity is determined via the inhibition of oviposition. 100% means that no tick has deposited eggs.

In this test, an activity of 100% was shown, for example, by the compound of Preparation Example I-1-a-1 at an exemplary active compound concentration of 20 μg/animal.

Example G

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2000 l of water/ha. After three weeks, the degree of damage to the plants is rated in % damage in comparison to the development of the untreated control. The figures denote:

0%=no action (like untreated control)

100%=total destruction

In this test, a damage of at least 80% to Alopecurus, Avena fatua and Setaria combined with good tolerance by soya beans was caused, for example by the compound of Preparation Example I-1-a-5 at an exemplary application rate of 125 g/ha.

96

What is claimed is:
1. Compounds of formula (I)

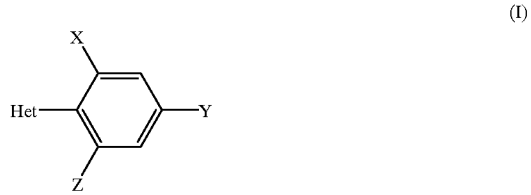

in which

X represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano, or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, Y represents hydrogen, halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano, Z represents hydrogen, halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano, where X does not represent halogen, $C_1$–$C_6$-alkyl, $C_1$–$C_6$-halogenoalkyl or $C_1$–$C_6$-alkoxy when Y represents hydrogen, halogen, $C_1$–$C_6$-alkyl, $C_1$–$C_6$-halogenoalkyl or $C_1$–$C_6$-alkoxy, Het represents

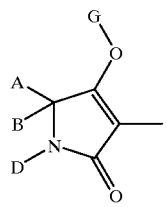

in which

A and B together with the carbon atom to which they are bonded represent cyclohexyl which is optionally substituted by fluorine, chlorine, bromine, $C_1$–$C_8$-alkyl, $C_1$–$C_8$-halogenoalkyl, $C_1$–$C_8$-alkoxy, $C_1$–$C_8$-alkylthio or phenyl, D represents hydrogen, or represents $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by halogen, or represents $C_3$–$C_8$-cycloalkyl in which up to two ring members are optionally replaced by oxygen and/or sulphur and which is optionally substituted by halogen, $C_1$–$C_4$-alkyl, $C_1$–$C_4$-alkoxy or $C_1$–$C_4$-halogenoalkyl, or represents phenyl, hetaryl having 5 or 6 ring atoms, phenyl-$C_1$–$C_6$-alkyl or hetaryl-$C_1$–$C_6$-alkyl having 5 or 6 ring atoms, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, G, represents hydrogen or represents one of the groups

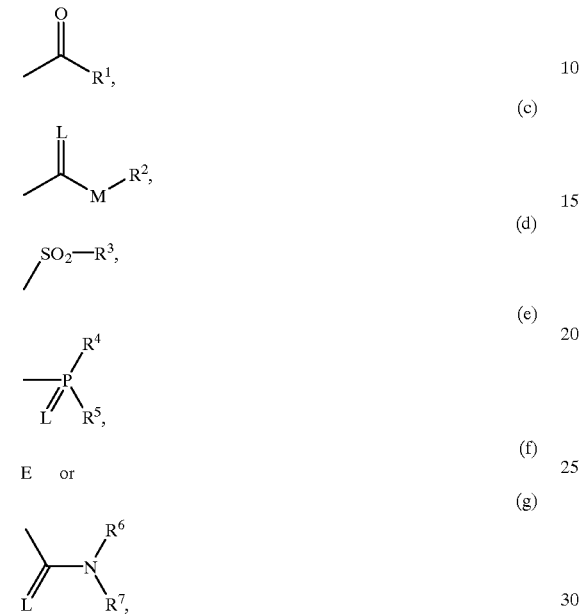

where

E represents a metal ion equivalent or an ammonium ion,

L represents oxygen or sulphur,

M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents $C_3$–$C_8$-cycloalkyl in which at least one ring member is optionally replaced by oxygen and/or sulphur and which is optionally substituted by halogen, $C_1$–$C_6$-alkyl or $C_1$–$C_6$-alkoxy, or phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or 5- or 6-membered hetaryl which is optionally substituted by halogen or $C_1$–$C_6$-alkyl, or phenoxy-$C_1$–$C_6$-alkyl which is optionally substituted by halogen or $C_1$–$C_6$-alkyl, or 5- or 6-membered hetaryloxy-$C_1$–$C_6$-alkyl which is optionally substituted by halogen, amino or $C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen, or $C_3$–$C_8$-cycloalkyl which is optionally substituted by halogen, $C_1$–$C_6$-alkyl or $C_1$–$C_6$-alkoxy, or phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents $C_1$–$C_8$-alkyl which is optionally substituted by halogen, or phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio or $C_3$–$C_7$-cycloalkylthio, each of which is optionally substituted by halogen, or phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen, or $C_1$–$C_8$-alkyl, $C_3$–$C_8$-cycloalkyl, $C_1$–$C_8$-alkoxy, $C_3$–$C_8$-alkenyl or $C_1$–$C_8$alkoxy-$C_1$–$C_8$-alkyl, each of which is optionally substituted by halogen, or phenyl which is optionally substituted by halogen, $C_1$–$C_8$-halogenoalkyl, $C_1$–$C_8$-alkyl or $C_1$–$C_8$-alkoxy, or benzyl which is optionally substituted by halogen, $C_1$–$C_8$-alkyl, $C_1$–$C_8$-halogenoalkyl or $C_1$–$C_8$-alkoxy, or together represent a $C_3$–$C_6$-alkylene radical in which one carbon atom is optionally replaced by oxygen or sulphur.

2. Compounds of the formula (I) according to claim 1 in which

X represents fluorine, chlorine, bromine, $C_1$–$C_4$-alkyl, $C_2$–$C_4$-alkenyl, $C_2$–$C_4$-alkinyl, $C_1$–$C_4$-alkoxy, $C_3$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_3$–$C_4$-halogenoalkenyl, $C_1$–$C_4$-halogenoalkoxy, $C_3$–$C_4$-halogenoalkenyloxy, nitro or cyano, or phenyl, phenoxy, phenylthio, benzyloxy or benzylthio, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano, Y represents hydrogen, fluorine, chlorine, bromine, $C_1$–$C_4$-alkyl, $C_2$–$C_4$-alkenyl, $C_2$–$C_4$-alkinyl, $C_1$–$C_4$-alkoxy, $C_3$–$C_4$-alkenyloxy, $C_1$–$C_4$-alkylthio, $C_1$–$C_4$-alkylsulphinyl, $C_1$–$C_4$-alkylsulphonyl, $C_1$–$C_4$-halogenoalkyl, $C_3$–$C_4$-halogenoalkenyl, $C_1$–$C_4$-halogenoalkoxy, $C_3$–$C_4$-halogenoalkenyloxy, nitro or cyano, Z represents hydrogen, fluorine, chlorine, bromine, $C_1$–$C_4$-alkyl, $C_2$–$C_4$-alkenyl, $C_2$–$C_4$-alkinyl, $C_1$–$C_4$-halogenoalkyl, $C_3$–$C_4$-halogenoalkenyl, $C_1$–$C_4$-alkoxy, $C_3$–$C_4$-alkenyloxy, $C_1$–$C_4$-halogenoalkoxy, $C_3$–$C_4$-halogenoalkenyloxy, nitro or cyano, where X does not represent halogen, $C_1$–$C_6$-alkyl, $C_1$–$C_6$-halogenoalkyl or $C_1$–$C_6$-alkoxy when Y represents hydrogen, halogen, $C_1$–$C_6$-alkyl, $C_1$–$C_6$-halogenoalkyl or $C_1$–$C_6$-alkoxy, D represents hydrogen, or $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, or $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl and in which one or two methylene groups which are not directly adjacent are optionally replaced by oxygen and/or sulphur, or phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, G, represents hydrogen or represents one of the groups

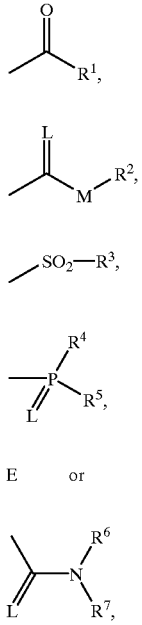

(b)

(c)

(d)

(e)

(f) E or (g)

in which
E represents a metal ion equivalent or an ammonium ion,
L represents oxygen or sulphur and
M represents oxygen or sulphur,
$R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or represents $C_3$–$C_7$-cycloalkyl which is optionally substituted by fluorine, chlorine,
  $C_1$–$C_5$-alkyl or $C_1$–$C_5$-alkoxy and in which up to two ring members are optionally replaced by oxygen and/or sulphur,
  or represents phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl,
  or phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy,
  or pyrazolyl, thiazolyl, pyridyl, pyrimidyl, furanyl or thienyl, each of which is optionally substituted by fluorine, chlorine, bromine or $C_1$–$C_4$-alkyl,
  or phenoxy-$C_1$–$C_5$-alkyl which is optionally substituted by fluorine, chlorine, brorrine or $C_1$–$C_4$-alkyl, or
  pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl,
$R^2$ represents $C_1$–$C_{16}$-alkyl, $C_2$–$C_{16}$-alkenyl, $C_1$–$C_6$-alkoxy-$C_2$–$C_6$-alkyl or -poly-$C_1$–$C_6$-alkoxy, each of which is optionally substituted by fluorine or chlorine,
  or $C_3$–$C_7$-cycloalkyl which is optionally substituted by fluorine, chlorine, $C_1$–$C_4$-alkyl or $C_1$–$C_4$-alkoxy, or phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy,
$R^3$ represents $C_1$–$C_6$-alkyl which is optionally substituted by fluorine or chlorine, or phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro,
$R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio or $C_3$–$C_6$-cycloalkylthio, each of which is optionally substituted by fluorine or chlorine, or phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalklyl,
$R^6$ and $R^7$ independently of one another represent hydrogen, or $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally substituted by halogen, or phenyl which is optionally substituted by halogen, $C_1$–$C_5$-halogenoalkyl, $C_1$–$C_5$-alkyl or $C_1$–$C_5$-alkoxy, or benzyl which is optionally substituted by halogen, $C_1$–$C_5$-alkyl, $C_1$–$C_5$-halogenoalkyl or $C_1$–$C_5$-alkoxy, or together represent a $C_3$–$C_6$-alkylene radical in which one carbon atom is optionally replaced by oxygen or sulphur.

3. Compounds of the formula (I) according to claim 1 in which
X represents fluorine, chlorine, bromine, methyl, ethyl, propyl, iso-propyl, vinyl, ethinyl, methoxy, ethoxy, propoxy, iso-propoxy, allyloxy, methallyloxy, trifluoromethyl, difluoromethoxy, trifluoromethoxy, methylthio, methylsulphinyl, methylsulphonyl, nitro, cyano, or phenyl, phenoxy, phenylthio, benzyloxy or benzylthio, each of which is optionally substituted by fluorine, chlorine, bromine, methyl, ethyl, propyl, iso-propyl, tert-butyl, methoxy, ethoxy, propoxy, tert-butoxy, trifluoromethyl, trifluoromethoxy, nitro or cyano,
Y represents hydrogen, fluorine, chlorine, bromine, methyl, ethyl, n-propyl, i-propyl, n-butyl, i-butyl, tert-butyl, vinyl, ethinyl, methoxy, ethoxy, propoxy, iso-propoxy, allyloxy, methallyloxy, trifluoromethyl, methylthio, methylsulphinyl, methylsulphonyl, difluoromethoxy, trifluoromethoxy, nitro or cyano,
Z represents hydrogen, fluorine, chlorine, bromine, methyl, ethyl, n-propyl, i-propyl, n-butyl, i-butyl, tert-butyl, vinyl, ethinyl, methoxy, ethoxy, propoxy, iso-propoxy, allyloxy, methallyloxy, difluoromethoxy, trifluoromethyl, trifluoromethoxy, nitro or cyano, where X does not represent halogen, $C_1$–$C_6$-alkyl, $C_1$–$C_6$-halogenoalkyl or $C_1$–$C_6$-alkoxy when Y represents hydrogen, halogen, $C_1$–$C_6$-alkyl, $C_1$–$C_6$-halogenoalkyl or $C_1$–$C_6$-alkoxy,
D represents hydrogen, or $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl, each of which is optionally substituted by fluorine or chlorine and in which one or two methylene groups which are not directly adjacent to each other are optionally replaced by oxygen and/or sulphur, or phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, G, represents hydrogen or represents one of the groups

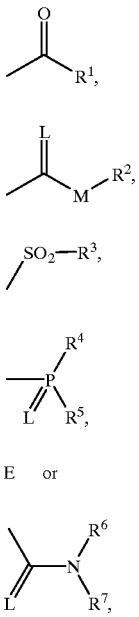

(b)

(c)

(d)

(e)

(f)

E or (g)

in which

E represents a metal ion equivalent or an ammonium ion,

L represents oxygen or sulphur and

M represents oxygen or sulphur, $R^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally substituted by fluorine or chlorine, or $C_3$–$C_6$-cycloalkyl which is optionally substituted by fluorine, chlorine, methyl, ethyl, propyl, i-propyl, butyl, i-butyl, tert-butyl, methoxy, ethoxy, propoxy or iso-propoxy and in which up to two ring members are optionally replaced by oxygen and/or sulphur, or phenyl which is optionally substituted by fluorine, chlorine, bromine, cyano, nitro, methyl, ethyl, propyl, 1-propyl, methoxy, ethoxy, trifluoromethyl, trifluoromethoxy, methylthio, ethylthio, methylsulphonyl or ethylsulphonyl, or benzyl which is optionally substituted by fluorine, chlorine, bromine, methyl, ethyl, propyl, i-propyl, methoxy, ethoxy, trifluoromethyl or trifluoromethoxy, or furanyl, thienyl, pyridyl, pyrimidyl, thiazolyl or pyrazolyl, each of which is optionally substituted by fluorine, chlorine, bromine, methyl or ethyl, or phenoxy-$C_1$–$C_4$-alkyl which is optionally substituted by fluorine, chlorine, methyl or ethyl, or pyridyl-oxy-$C_1$–$C_4$-alkyl, pyrimidyloxy-$C_1$–$C_4$alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl, poly-$C_2$–$C_4$-alkoxy-$C_2$–$C_6$-alkyl, each of which is optionally substituted by fluorine or chlorine, or $C_3$–$C_6$-cycloalkyl which is optionally substituted by fluorine, chlorine, methyl, ethyl, propyl, iso-propyl or methoxy, or phenyl or benzyl, each of which is optionally substituted by fluorine, chlorine, cyano, nitro, methyl, ethyl, propyl, i-propyl, methoxy, ethoxy, trifluoromethyl or trifluoromethoxy, $R^3$ represents methyl, ethyl, propyl or isopropyl, each of which is optionally substituted by fluorine or chlorine, or phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl, $R^6$ and $R^7$ independently of one another represent hydrogen, or $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally substituted by fluorine or chlorine, or phenyl which is optionally substituted by fluorine, chlorine, bromine, $C_1$–$C_4$-halogenoalkyl, $C_1$–$C_4$-alkyl or $C_1$–$C_4$-alkoxy, or benzyl which is optionally substituted by fluorine, chlorine, bromine, $C_1$–$C_4$-alkyl, $C_1$–$C_4$-halogenoalkyl or $C_1$–$C_4$-alkoxy, or together represent a $C_5$–$C_6$-alkylene radical in which one carbon atom is optionally replaced by oxygen or sulphur.

4. A compound according to claim 1, which has the formula:

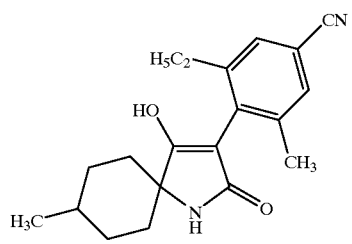

5. A process for preparing a compound according to claim 1, which has the formula:

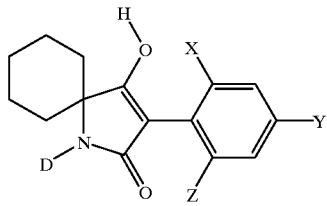

in which

D, X, Y and Z are as defined in claim 1;

said process comprising subjecting an N-acylamino acid ester of the formula:

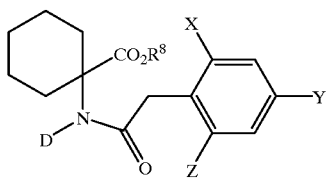

in which

D, X, Y and Z are as defined in claim 1; and $R^8$ represents alkyl;

to an intramolecular condensation reaction in the presence of a diluent and in the presence of a base.

6. A composition comprising at least one compound of the formula (I) according to claim 1 and a carrier.

7. A method of combating pests comprising applying to said pests or their habitat a pesticidally effective amount of at least one compound of the formula (I) according to claim 1.

8. A method of combating weeds comprising applying to said weeds or their environment a herbicidally effective amount of at least one compound of the formula (I) according to claim 1.

9. A composition comprising at least one compound of the formula (I) according to claim 4, and a carrier.

10. A method of combating pests comprising applying to said pests or their habitat a pesticidally effective amount of at least one compound of the formula (I) according to claim 4.

11. A method of combating weeds comprising applying to said weeds or their environment a herbicidally effective amount of at least one compound of the formula (I) according to claim 4.

* * * * *